(12) United States Patent
Bellows et al.

(10) Patent No.: US 12,121,408 B2
(45) Date of Patent: Oct. 22, 2024

(54) PARALLELISM ADJUSTMENT MECHANISM FOR LOAD BALANCING ARM

(71) Applicant: American Sterilizer Company, Mentor, OH (US)

(72) Inventors: Lance Bellows, Painesville, OH (US); Michael Hollopeter, Kirtland, OH (US); Martin Kraig, Mentor, OH (US); Brad Lachmeier, Chesterland, OH (US); Jerime Pichler, Painesville, OH (US); Nicholas Puterbaugh, Mentor, OH (US); David Westenfelder, Mantua, OH (US); Robert Chavez, Montgomery, AL (US)

(73) Assignee: American Sterilizer Company, Mentor, OH (US)

( * ) Notice: Subject to any disclaimer, the term of this patent is extended or adjusted under 35 U.S.C. 154(b) by 447 days.

(21) Appl. No.: 17/511,827

(22) Filed: Oct. 27, 2021

(65) Prior Publication Data

US 2022/0133431 A1    May 5, 2022

Related U.S. Application Data

(60) Provisional application No. 63/107,640, filed on Oct. 30, 2020.

(51) Int. Cl.
*F16M 11/00* (2006.01)
*A61B 90/50* (2016.01)

(52) U.S. Cl.
CPC ...... *A61B 90/50* (2016.02); *A61B 2090/5025* (2016.02); *A61B 2090/506* (2016.02)

(58) Field of Classification Search
CPC ............ A61B 90/50; A61B 2090/5025; A61B 2090/506; A61G 12/004
See application file for complete search history.

(56) References Cited

U.S. PATENT DOCUMENTS 2,299,251 A    10/1942  Perbal
3,240,925 A *  3/1966  Paschke .............. F21V 33/0068
                                                362/253

(Continued)

FOREIGN PATENT DOCUMENTS

WO          01/90630 A1    11/2001

OTHER PUBLICATIONS

International Search Report and Written Opinion for corresponding International Application No. PCT/US2021/056766 mailed Feb. 25, 2022.

*Primary Examiner* — Amy J. Sterling
(74) *Attorney, Agent, or Firm* — Renner, Otto, Boisselle & Sklar, LLP

(57) ABSTRACT

A load balancing arm for a medical device support system includes a proximal hub, a support arm, a link, and a distal end vertical block. The components together may form a four bar linkage. The proximal hub is configured for pivotable movement about an axis P-P. The distal hub is configured to support a medical device load for pivotable movement about an axis D-D. The distal hub is mounted to the distal end vertical block for pivotable movement between a first position in which the axis D-D is at a first angle relative to the axis P-P and a second position in which the axis D-D is at a second angle relative to the axis P-P, wherein the first angle is different than the second angle. A parallelism adjustment mechanism enables the axis D-D to be adjusted so as to be substantially parallel to the axis P-P.

21 Claims, 23 Drawing Sheets

(56) References Cited

U.S. PATENT DOCUMENTS

| | | | |
|---|---|---|---|
| 4,215,972 | A | 8/1980 | Yamasaki et al. |
| 5,597,939 | A | 12/1997 | Kubota |
| 6,328,458 | B1 * | 12/2001 | Bell ........................ F21V 21/26 |
| | | | 403/150 |
| 6,364,268 | B1 | 4/2002 | Metelski |
| 6,471,457 | B2 | 10/2002 | Nago |
| 6,921,056 | B2 | 7/2005 | Holung |
| 7,097,145 | B2 | 8/2006 | Turner |
| 8,276,867 | B2 | 10/2012 | Hung |
| 8,424,833 | B2 * | 4/2013 | Muller ............... F16M 11/2064 |
| | | | 362/147 |
| 9,022,339 | B2 * | 5/2015 | Borg ................... H02G 3/0493 |
| | | | 248/323 |
| 9,433,736 | B2 | 9/2016 | Smith et al. |
| 9,581,276 | B2 | 2/2017 | Crum et al. |
| 9,822,922 | B2 | 11/2017 | Doi et al. |
| 10,080,696 | B2 | 9/2018 | Oginski et al. |
| 10,216,070 | B2 | 2/2019 | Wood |
| 11,131,423 | B2 * | 9/2021 | Anderson ............... F16M 11/10 |
| 2002/0139913 | A1 * | 10/2002 | Kummerfeld ........... F21V 21/26 |
| | | | 248/343 |
| 2007/0080275 | A1 | 4/2007 | Stachowski et al. |
| 2009/0140114 | A1 | 6/2009 | Blackburn |
| 2013/0313382 | A1 | 11/2013 | Jakubczak et al. |
| 2019/0250251 | A1 | 8/2019 | Gibson et al. |
| 2020/0246109 | A1 | 8/2020 | Pichler et al. |
| 2020/0246110 | A1 | 8/2020 | Pichler et al. |

* cited by examiner

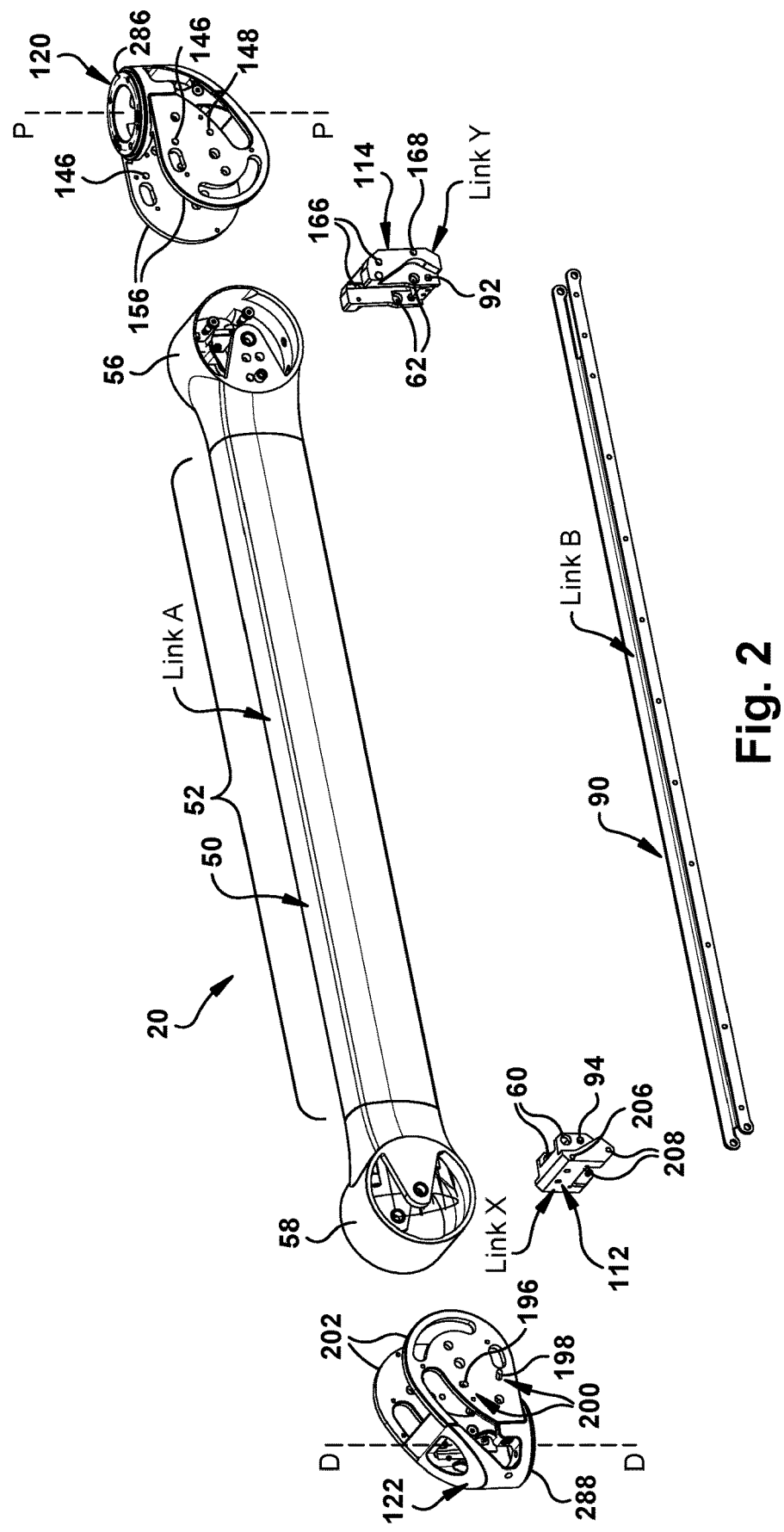

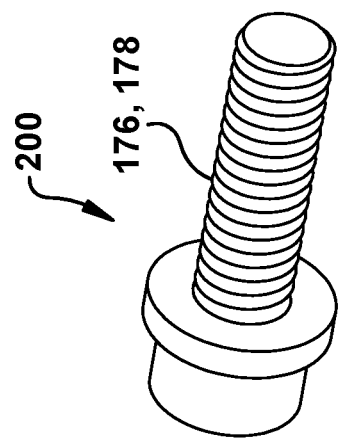
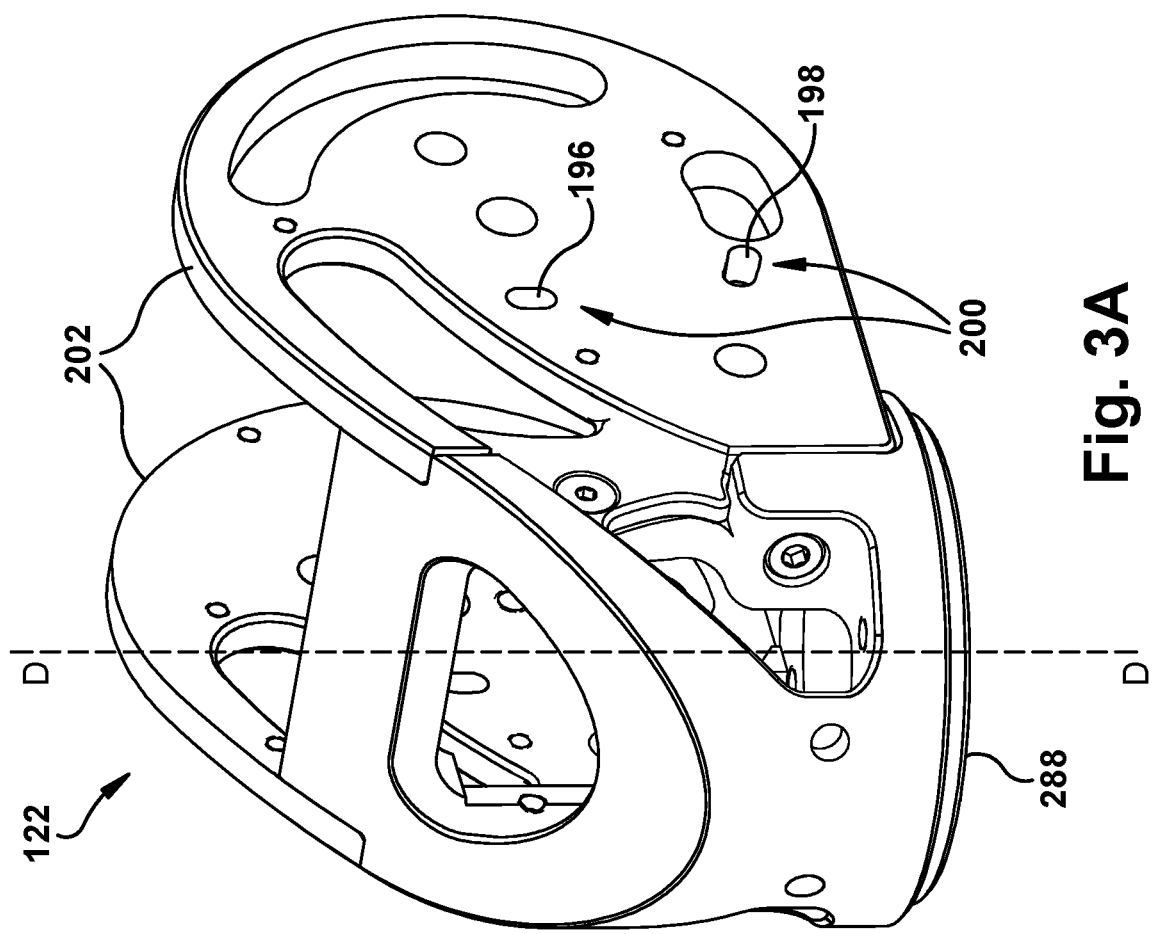

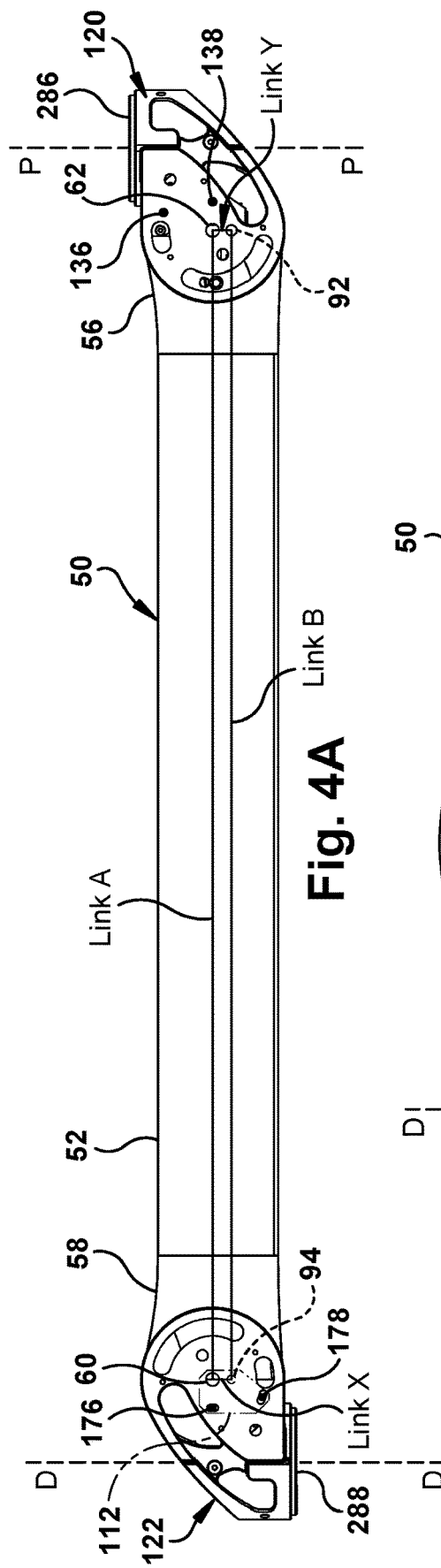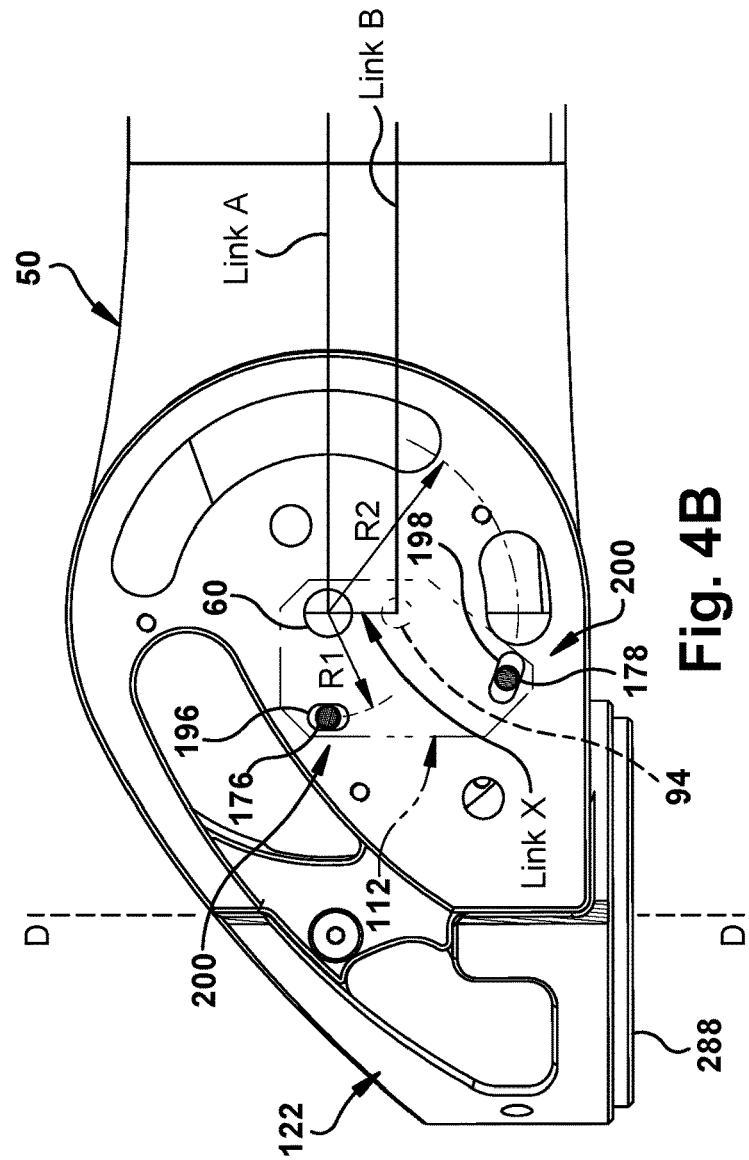

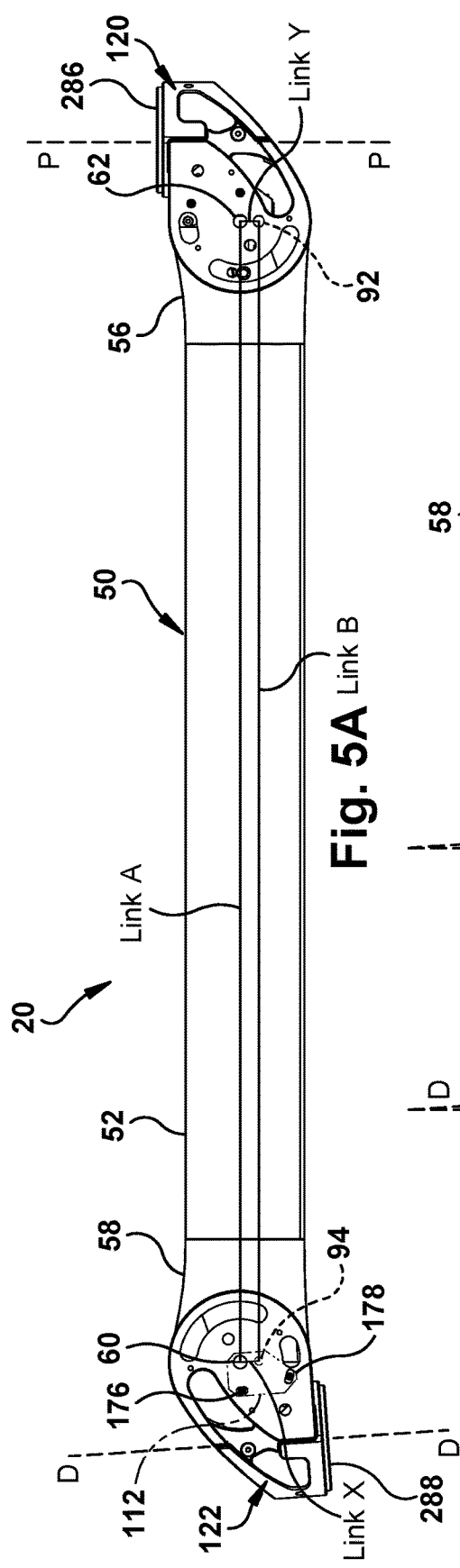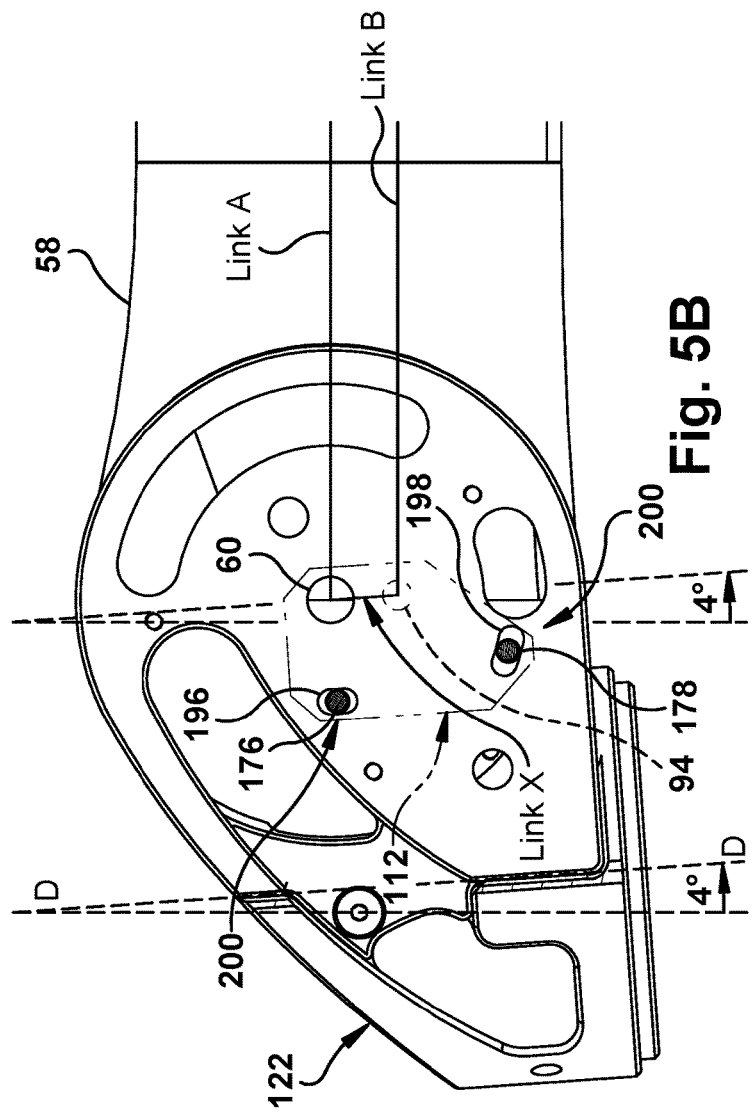

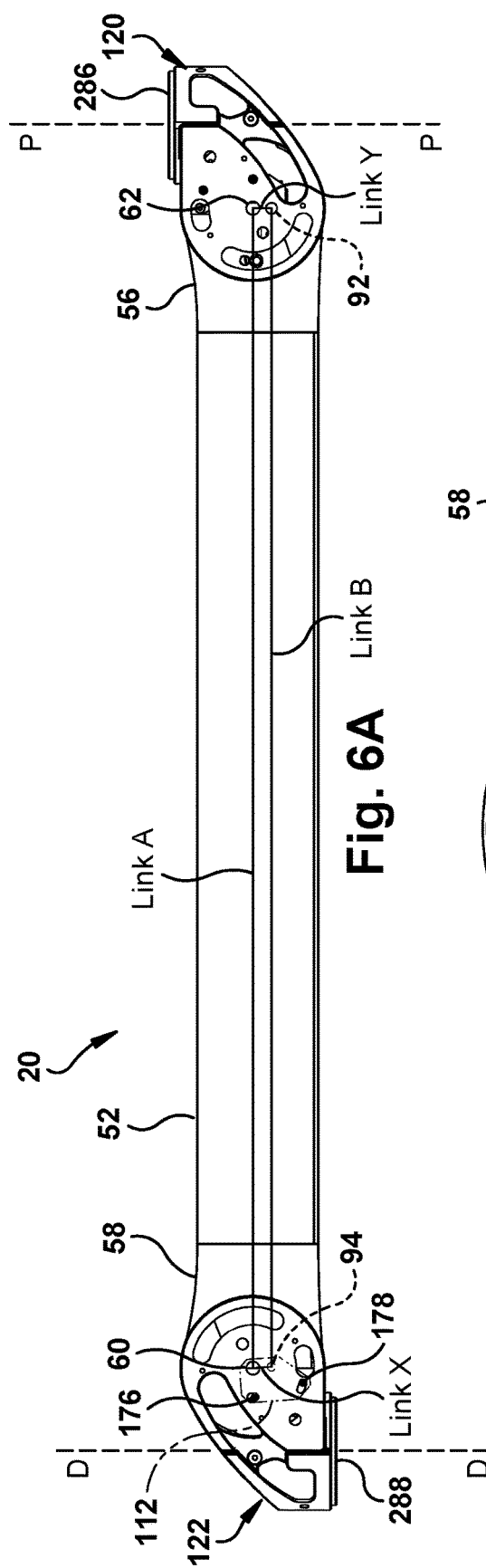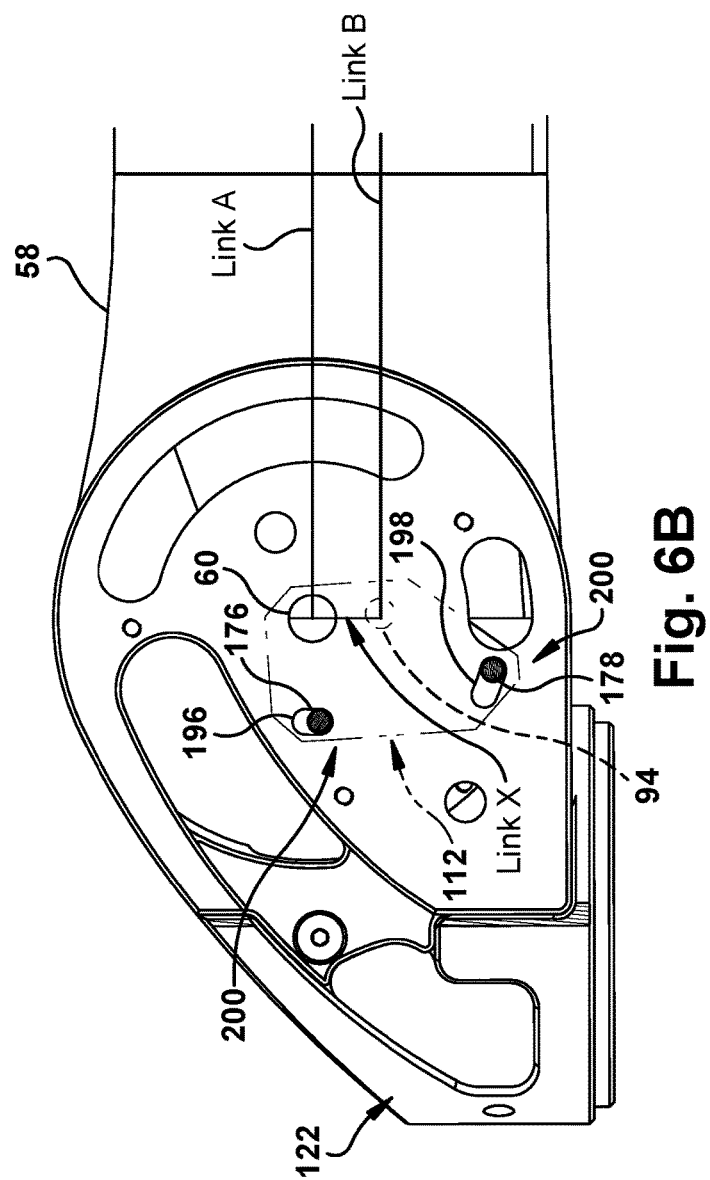

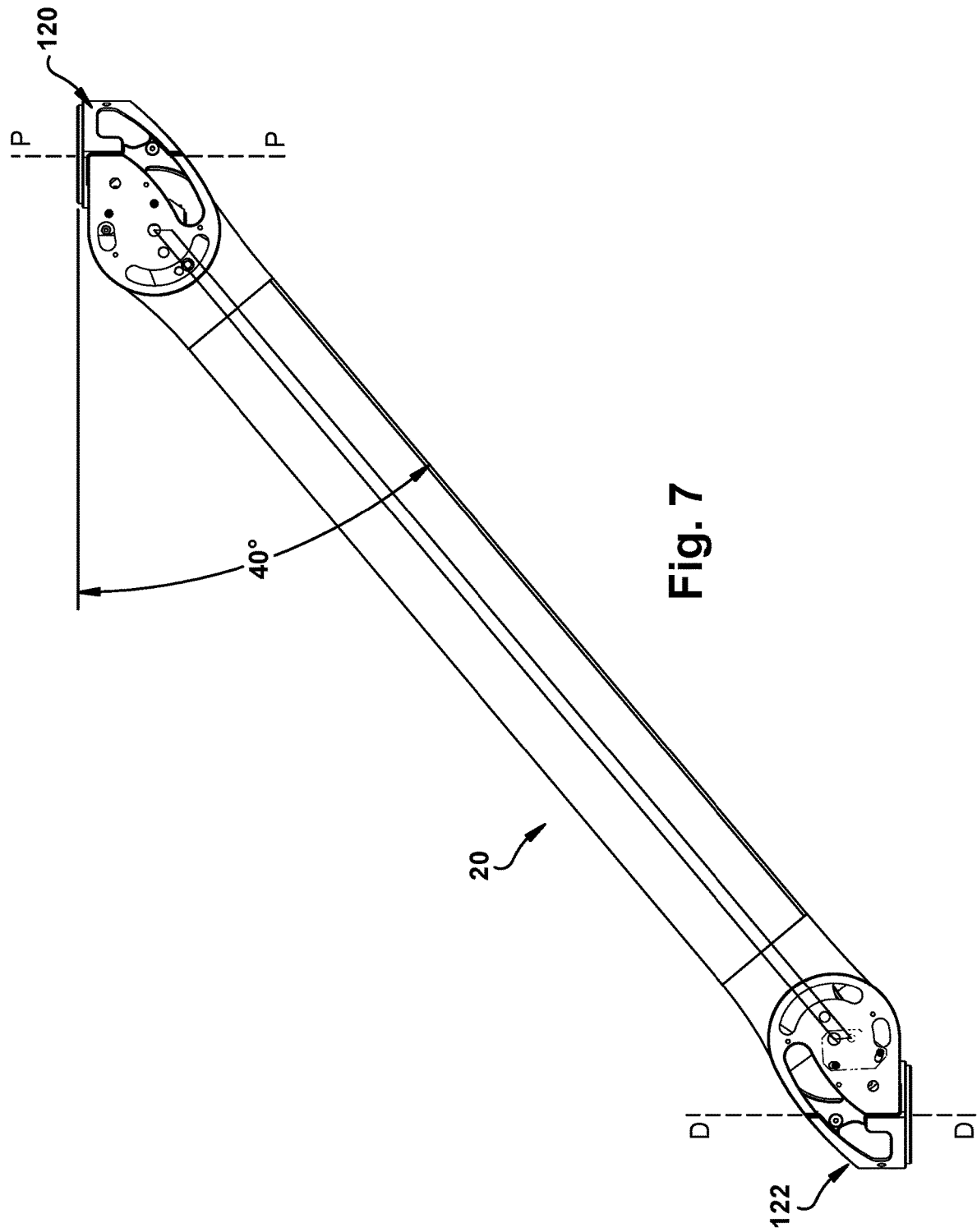

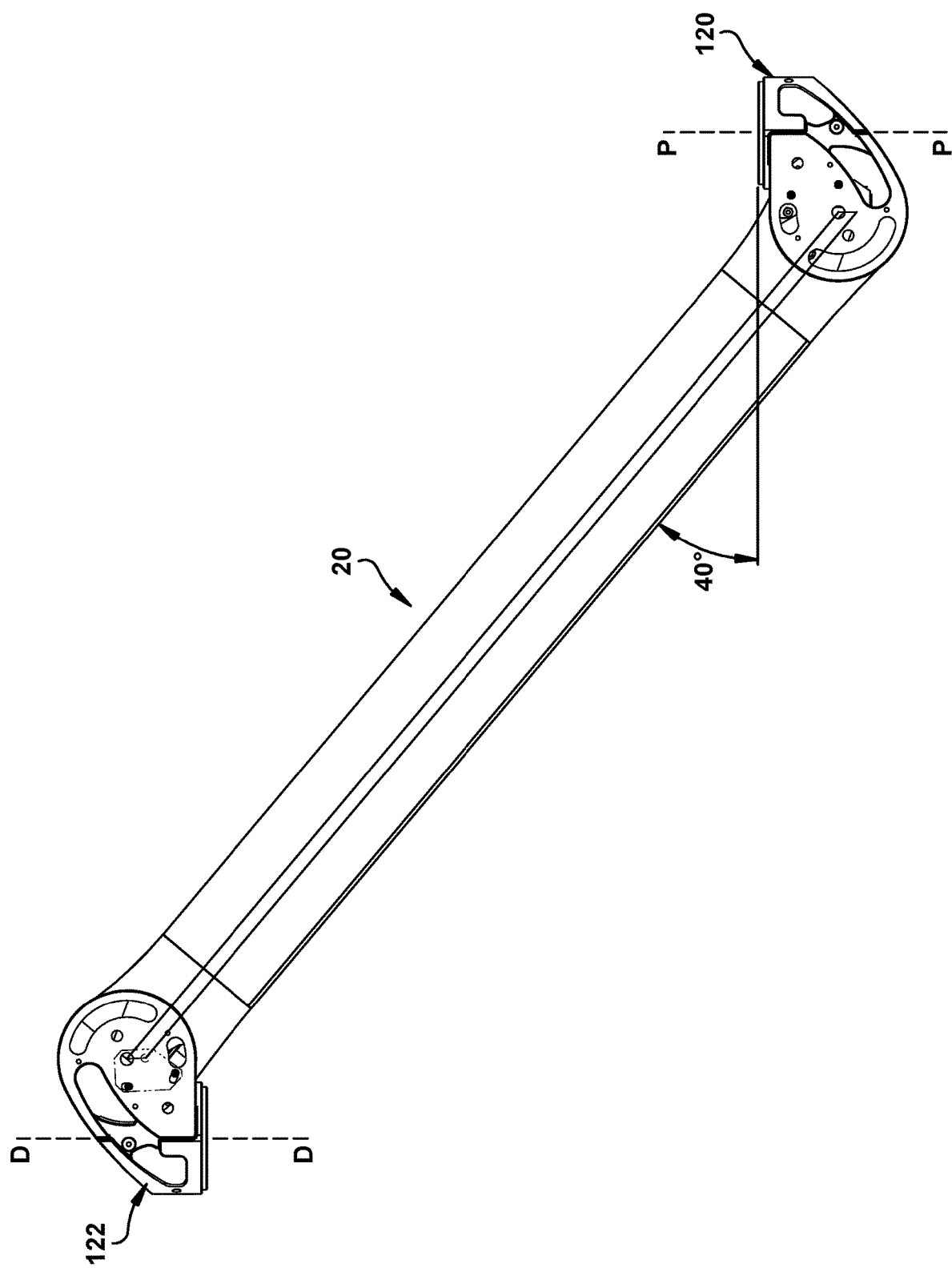

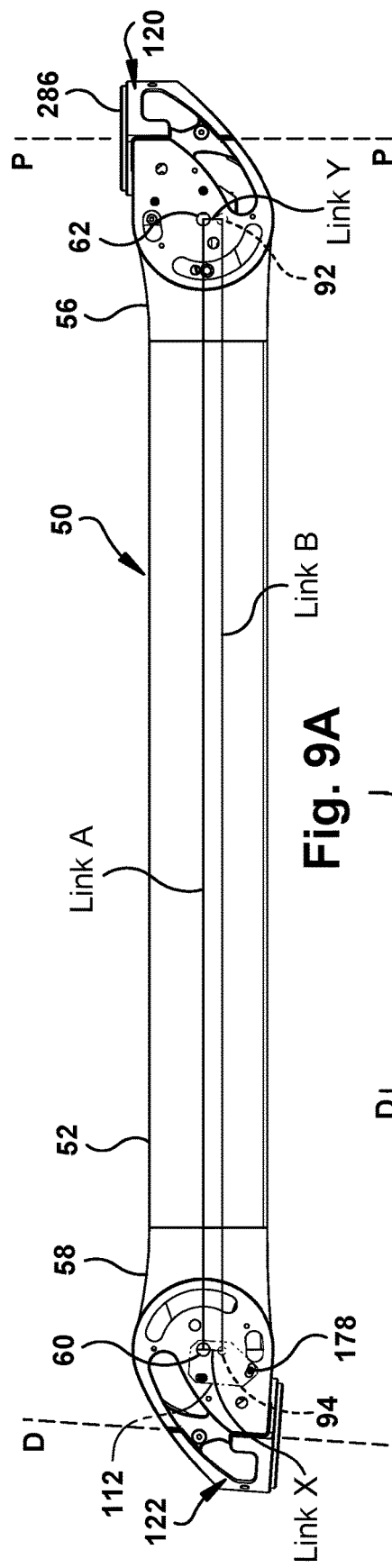
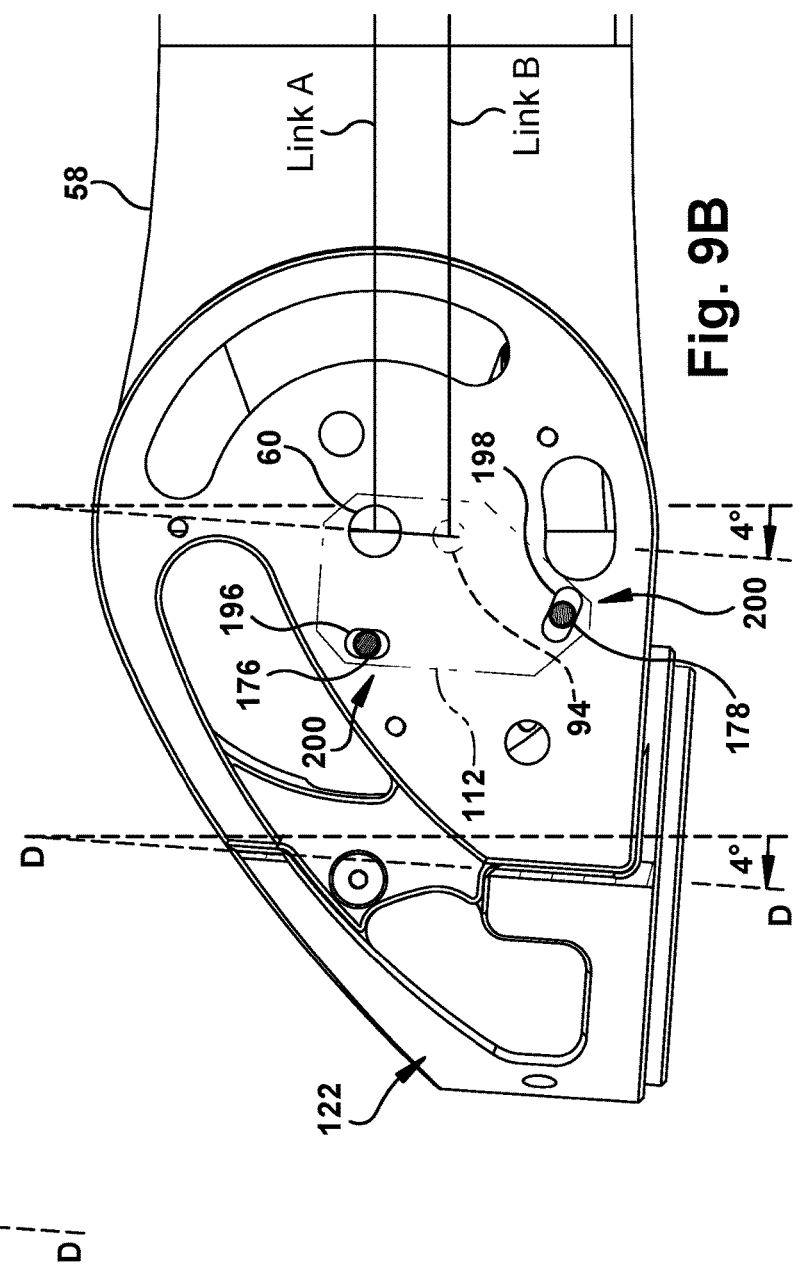
Fig. 9A
Fig. 9B

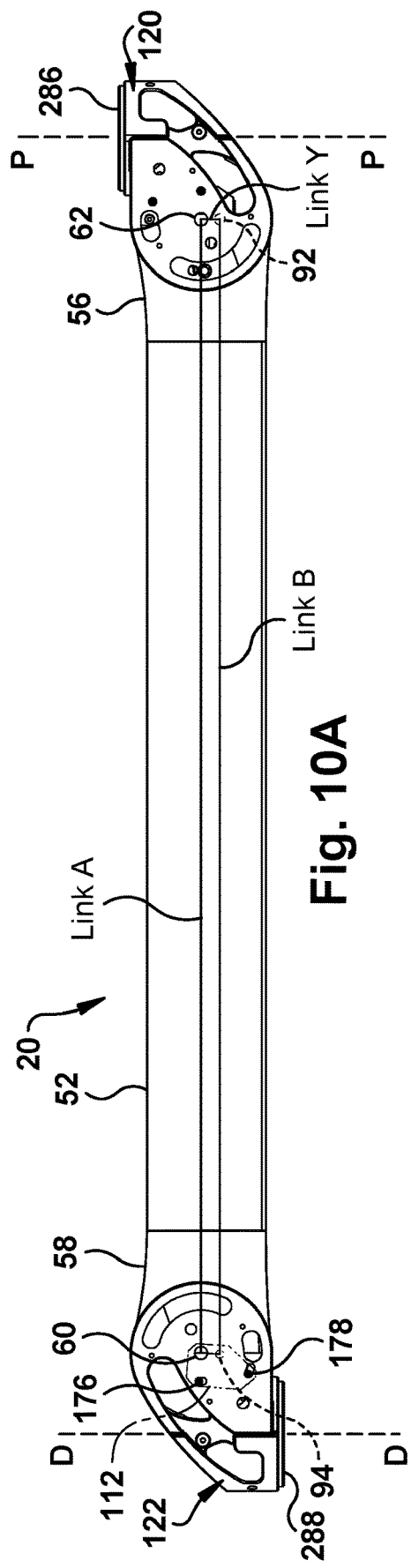
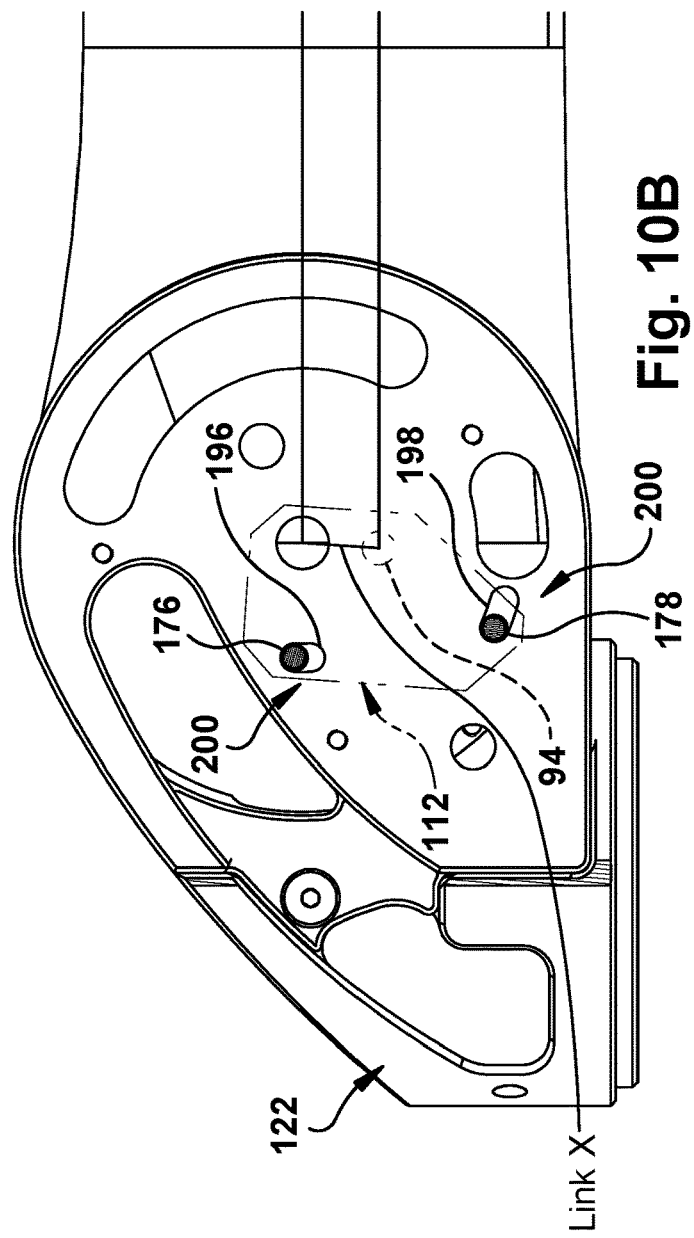
Fig. 10A
Fig. 10B

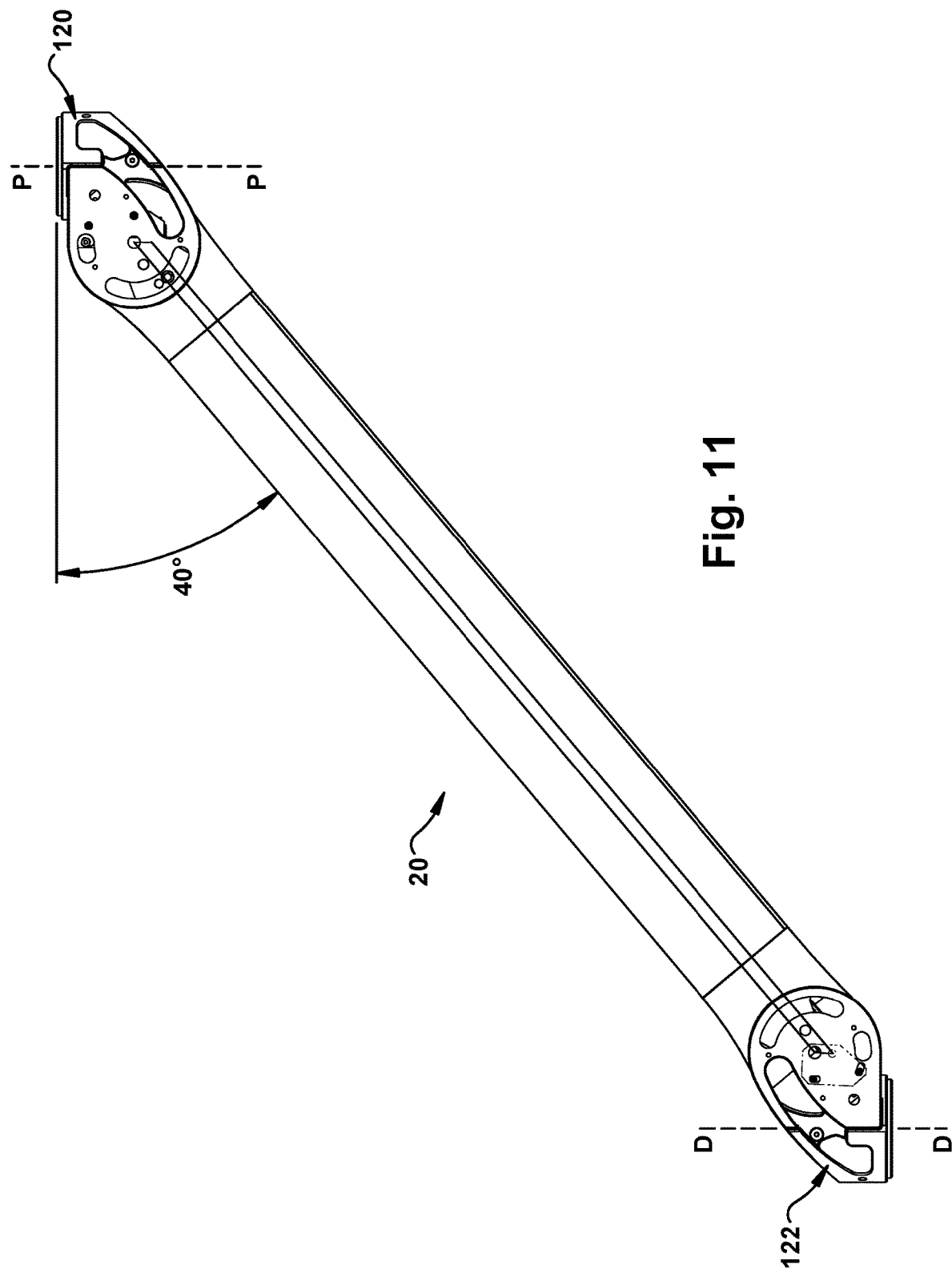

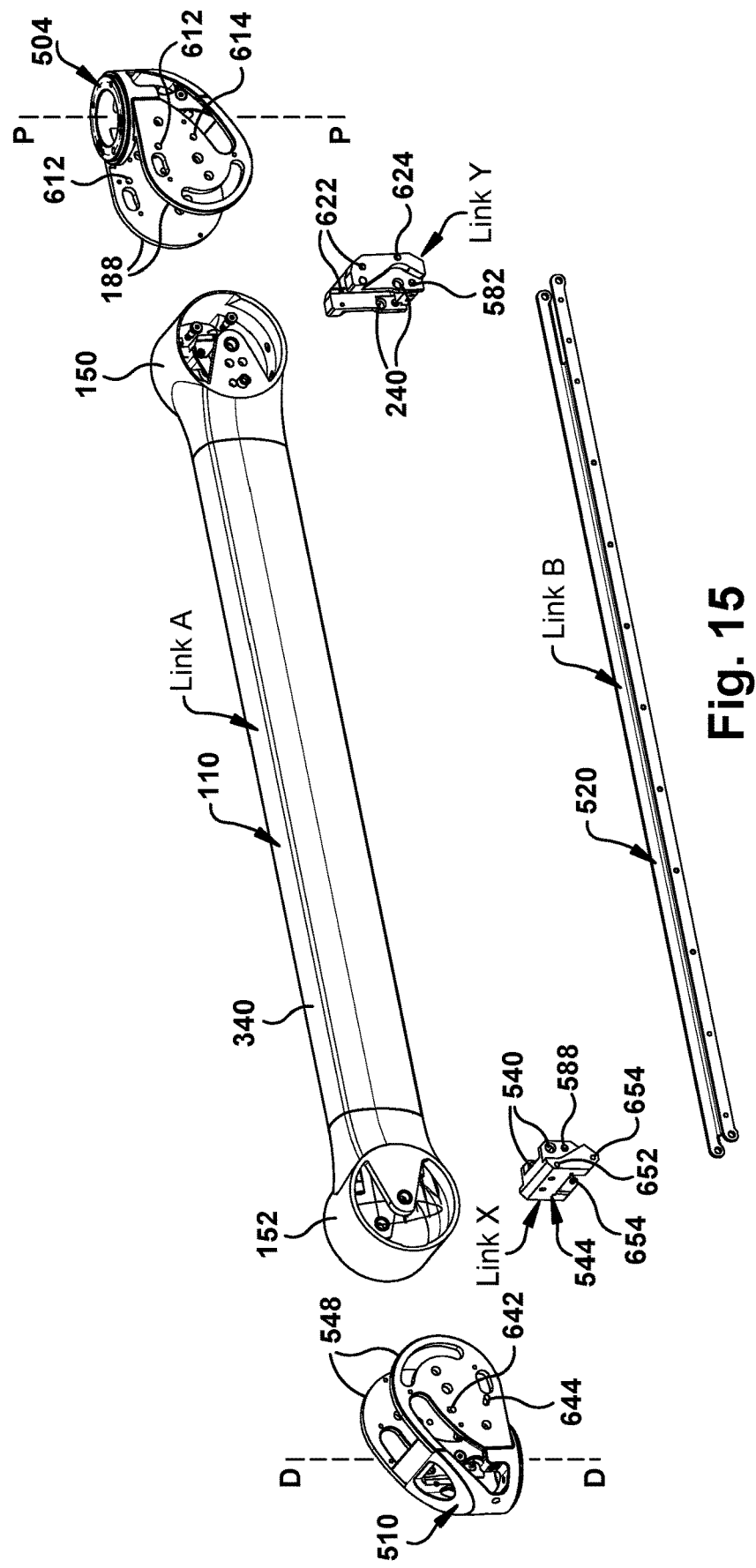

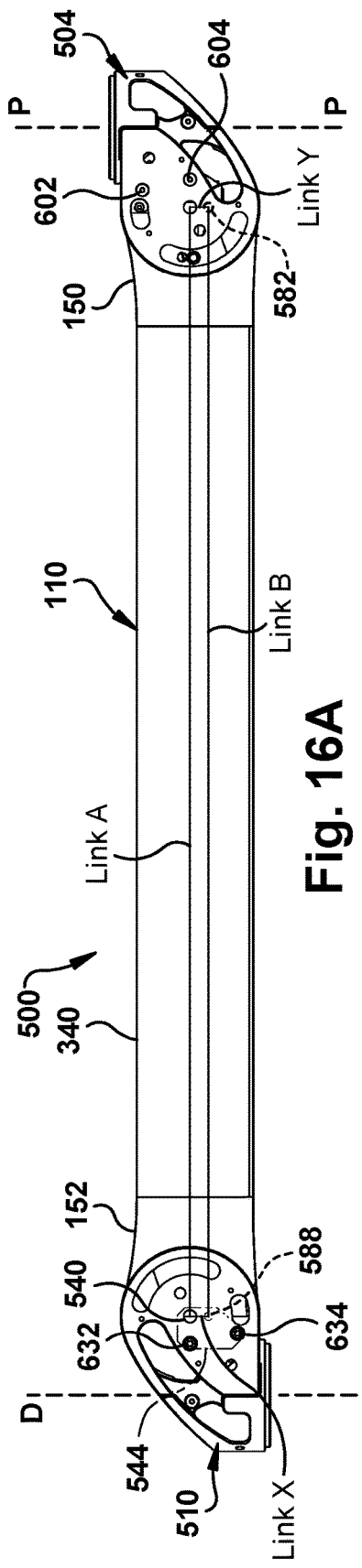
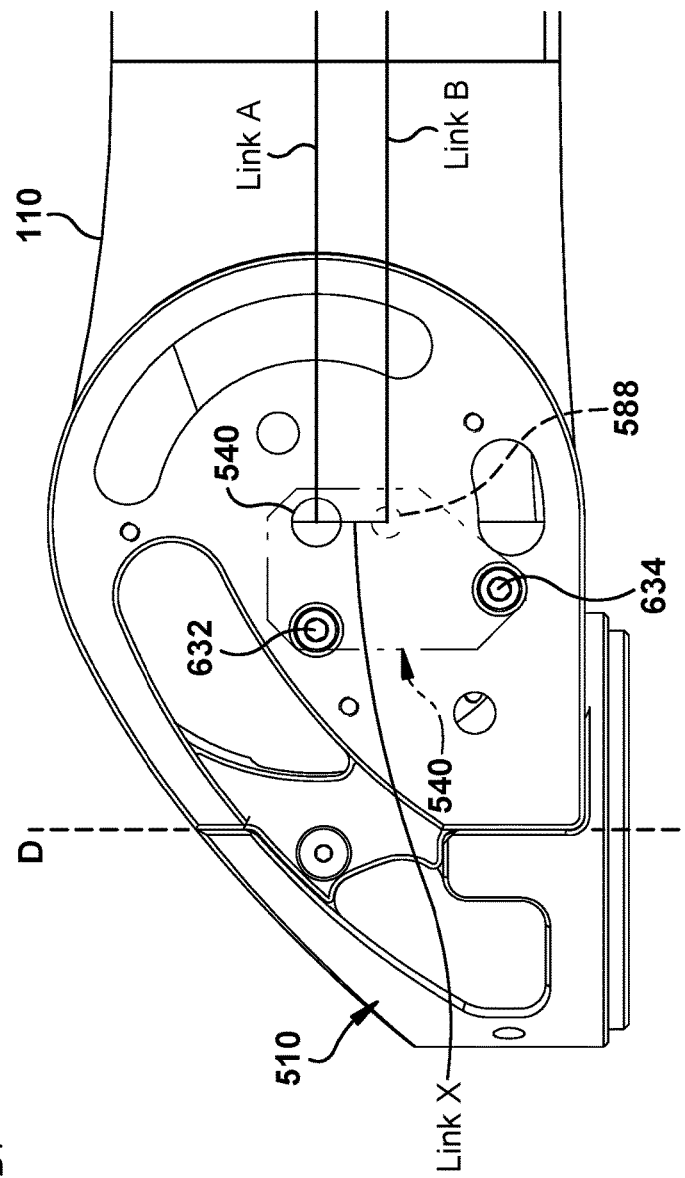
Fig. 16A
Fig. 16B

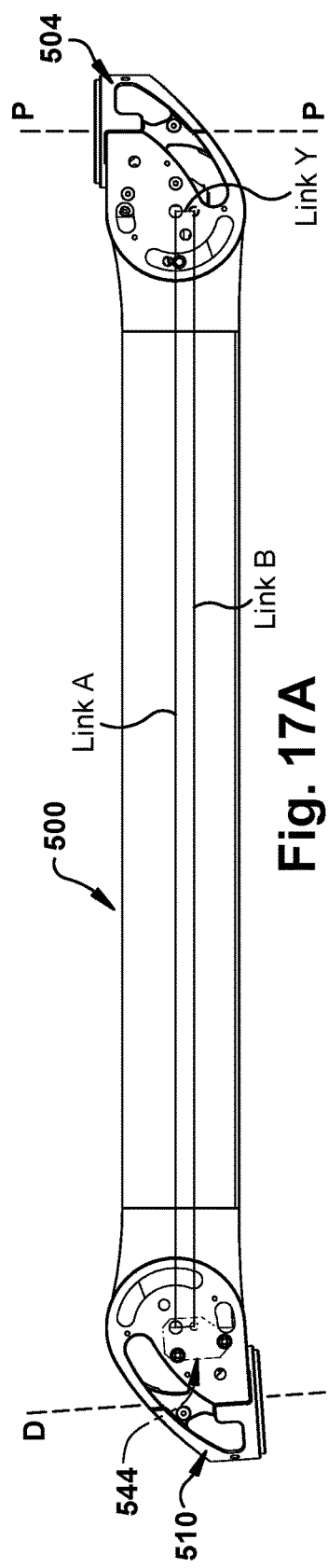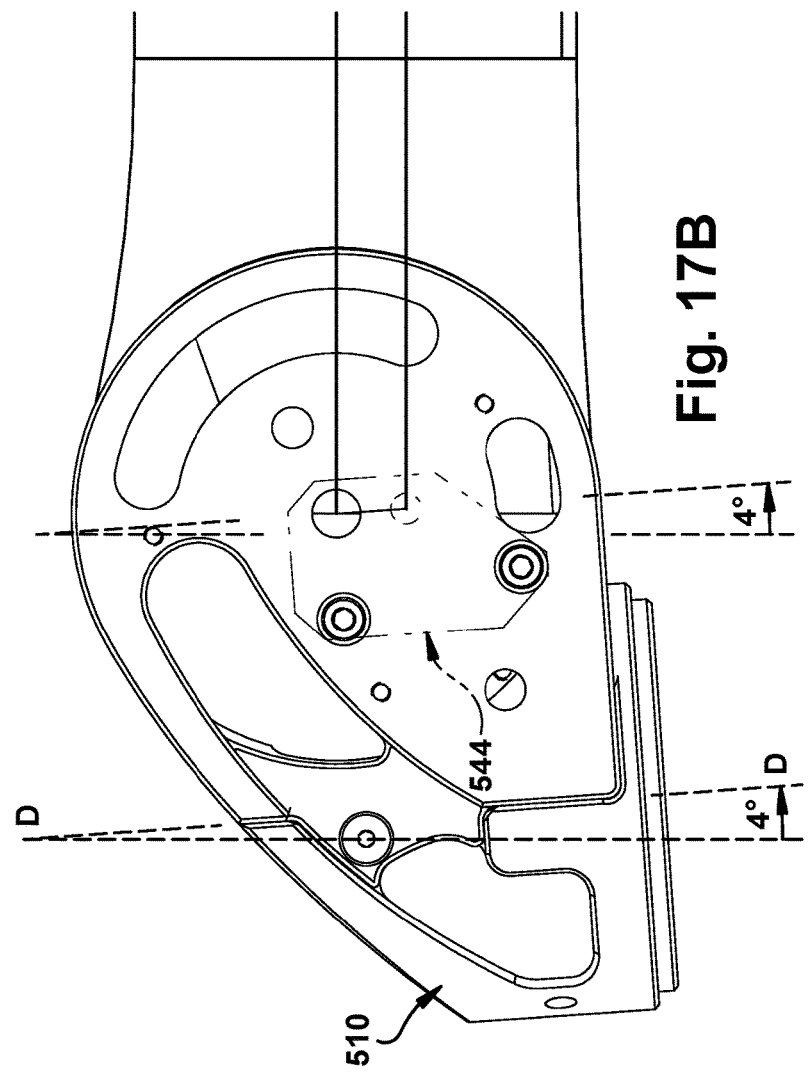

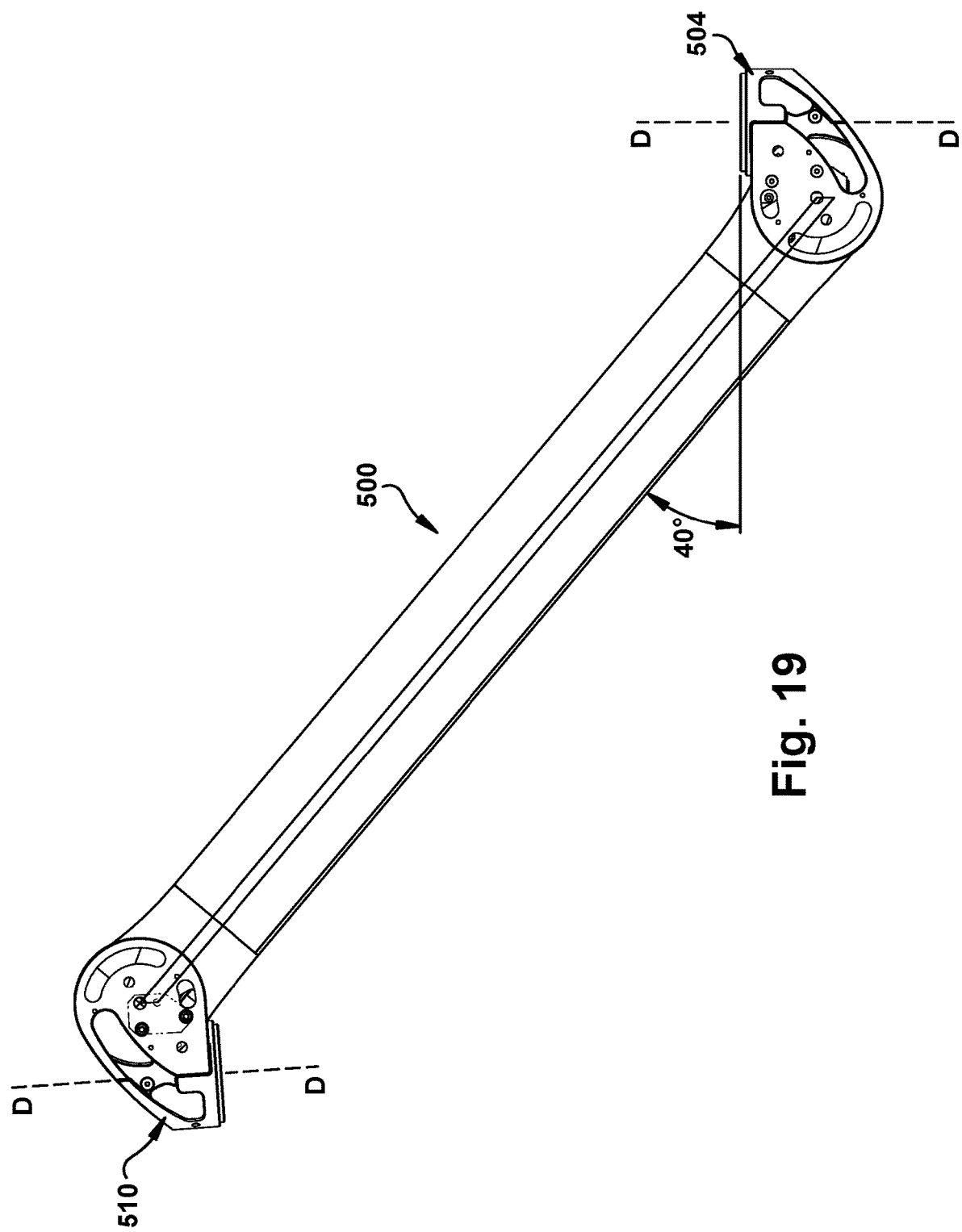

PARALLELISM ADJUSTMENT MECHANISM FOR LOAD BALANCING ARM

This application claims the benefit of U.S. Provisional Application No. 63/107,640 filed Oct. 30, 2020, which is hereby incorporated herein by reference in its entirety.

FIELD OF INVENTION

This application relates generally to a load balancing arm for a medical device support system or carry system for use in, for example, a hospital examination room, a clinic, a surgery room or an emergency room, and more particularly to a load balancing arm that includes a parallelism adjustment mechanism for ensuring that an axis about which a medical device load pivots and an axis about which a proximal end hub of the load balancing arm pivots are parallel.

BACKGROUND

Medical device support systems, also referred to as suspension systems and carry systems, are used in health treatment settings such as hospital examination rooms, clinics, surgery rooms and emergency rooms. These systems may suspend or support any variety of medical devices or components including surgical lights, supply consoles, patient monitors, camera detector heads, medical instruments, ventilator systems, suction devices, among others. The support systems typically include a vertically oriented shaft or support column that is suspended from the ceiling or mounted to a wall, one or more generally horizontal extension arms mounted for rotational movement about the shaft, and one or more load balancing arms, also known as counterbalancing arms or spring arms, that enable positioning of a medical device to a proper orientation relative to for example a patient operating table and healthcare professionals in the operating room.

Referring to FIGS. 15-20B, a load balancing arm 500 may include a four bar, four pin joint linkage construction desirably in the form of a parallelogram. The four bar linkage is formed by lateral Links A and B, and upright Links X and Y at opposite ends of the lateral Links A and B. Link A is a support arm 110 and may be constructed of an intermediate beam 340, and a proximal end inner hub 150 and a distal end inner hub 152 at opposite ends of the intermediate beam 340, where the Link A extends between pivot pins 540 and pivot pins 240. A powder coating layer may be provided on the proximal end inner hub 150 and distal end inner hub 152. The Link A components may be sandwiched together with tension members, for example, tie rods. Link B may be constructed as a parallel link assembly 520 between the pivot pin 582 and the pivot pin 588, made up of three components spot-welded together; that is, a U-shape stainless steel member and a pair of parallel relatively harder stainless steel side braces spot welded to the U-shape stainless steel member. Link X may be in the form of a distal end vertical block 544 between the pin 588 and the pins 540. Link Y may be made up of a load adjustment base 530 between the pins 240 and the pin 582.

The load balancing arm 500 may also include a proximal end outer hub 504 and a distal end outer hub 510. The proximal end outer hub 504 may be fastened to the load adjustment base 530 by means of fasteners 602, 604. More specifically, the fasteners 602, 604 are inserted through through-holes 612, 614 in vertically oriented opposite side walls 188 of the proximal end outer hub 504 and threaded into threaded holes 622, 624 in opposite side walls of the load adjustment base 530. The distal end outer hub 510 may be fastened to the distal end vertical block 544 by means of fasteners 632, 634. More specifically, the fasteners 632, 634 are inserted through through-hole openings 642, 644 in vertically oriented opposite side walls 548 of the distal end outer hub 510 and threaded into threaded holes 652, 654 in opposite side walls of the distal end vertical block 544.

The proximal end outer hub 504 is pivotably mounted about an axis P-P to the distal end of the extension arm. The axis P-P desirably is parallel to the vertically aligned pins 240, 582 of the load adjustment base 530. A medical device load such as a patient monitor or the like is pivotably mounted about an axis D-D to the distal end outer hub 510. The axis D-D desirably is parallel to the vertically aligned pins 540, 588 of the distal end vertical block 544. The support arm 110 is pivotable at its proximal end inner hub 150 about a main pivot axis defined by the centers of the pivot pins 240 of the load adjustment base 530. The support arm 110 is pivotable at its distal end inner hub 152 about a pivot axis defined by the centers of the pivot pins 540 of the distal end vertical block 544. The parallel link assembly 520 is pivotable at its proximal end about a pivot axis defined by the centers of the pivot pins 582, and pivotable at its distal end about a pivot axis defined by the centers of the pivot pins 588.

In the four bar linkage of the above load balancing arm 500, it is desirable that the Link A and Link B lengths are equal and the Link X and Link Y lengths are equal. In this way, the vertically aligned pins 540, 588 and the axis D-D of the distal end outer hub 510 remain parallel to the vertically aligned pins 240, 582 and the axis P-P of the proximal end outer hub 504 throughout the pivotable range of the load balancing arm 500 about the main pivot axis. Such accurate alignment in the four bar linkage permits the medical device load mounted to the distal end outer hub 510 of the load balancing arm 500 to remain properly oriented regardless of its vertical displacement from the ceiling of the operating room.

For some load balancing arms, however, it may be difficult to ensure the axis D-D of the distal end outer hub 510 remains aligned relative to, for example parallel to, the axis P-P of the proximal end outer hub 504. The inventors have found, for example, that there may be instances where the stack up of manufacturing tolerances cause unequal lengths in Links X and Y and/or in Links A and B, resulting in nonoptimal or less than desirable alignment of the vertical axes of the respective distal end outer hub 510 and proximal end outer hub 504.

Accordingly, there remains a need for further contributions in this area of technology.

SUMMARY OF INVENTION

The application relates to a load balancing arm, also known as a counterbalancing arm or spring arm, for a medical device support system, in which the load balancing arm utilizes a parallelism adjustment mechanism to ensure that an axis about which a medical device load pivots and an axis about which a proximal end hub of the load balancing arm pivots are parallel.

According to one aspect of the invention, a load balancing arm for a medical device support system includes a proximal hub configured for pivotable movement about an axis P-P; a support arm having a proximal end and a distal end, the proximal end of the support arm being pivotably mounted to the proximal hub about a support arm proximal end pivot axis; a link having a proximal end and a distal end, the proximal end of the link being pivotably mounted to the proximal hub about a link proximal end pivot axis; a distal end vertical block pivotably mounted to the distal end of the support arm about a support arm distal end pivot axis and pivotably mounted to the distal end of the link about a link distal end pivot axis; and a distal hub configured to support a medical device load for pivotable movement about an axis D-D; wherein the distal hub is mounted to the distal end vertical block for pivotable movement between a first position in which the axis D-D is at a first angle relative to the axis P-P and a second position in which the axis D-D is at a second angle relative to the axis P-P, wherein the first angle is different than the second angle.

Embodiments of the invention may include one or more of the following additional features separately or in combination.

The proximal hub, the support arm, the link, and the distal end vertical block may form a four bar linkage.

The distal hub may be mounted to the distal end vertical block for pivotable movement about the support arm distal end pivot axis.

The support arm proximal end pivot axis and the link proximal end pivot axis may be substantially vertically aligned and the support arm distal end pivot axis and the link distal end pivot axis may be substantially vertically aligned.

The load balancing arm may be configured such that when the distal hub is in the first position the axis D-D is not parallel to the axis P-P and when the distal hub is in the second position the axis D-D is substantially parallel to the axis P-P.

The axis P-P may be a vertical axis P-P and the load balancing arm may be configured such that when the distal hub is in the second position the axis D-D is a predetermined amount of degrees offset from the vertical axis P-P to compensate for assembly deflection resulting from the medical device load.

The distal hub may include a slot opening and the distal end vertical block may have a fastener projecting therefrom that extends into the slot opening, and the distal hub may be configured such that as the distal hub is pivotably moved from the first position to the second position the slot opening moves along the fastener projecting therein.

Opposite ends of the slot opening may define maximum pivotable movement of the distal hub relative to the distal end vertical block.

The fastener may be a threaded fastener and the distal end vertical block may have a threaded hole for threadingly receiving the fastener, and the fastener may have a head that is sufficiently wide to bridge the slot opening and that is configured when tightened to engage the distal hub on opposite sides of the slot opening to secure the distal hub to the distal end vertical block.

The fastener may secure the distal hub to the distal end vertical block by means of friction provided by a clamp load of the fastener head exerted on the distal hub.

The fastener may include a serrated flange screw and the size of the serrated flange screw and the materials of the serrated flange screw and distal hub may be selected so that the serrated flange screw when tightened to a predetermined torque displaces some material in the distal hub to create a mechanical interference lock between a head of the serrated flange screw and the distal hub.

The support arm may include a support arm proximal end hub and a support arm distal end hub and an intermediate beam between the support arm proximal end hub and the support arm distal end hub, and the support arm proximal end hub may be pivotably mounted to the proximal hub, and the distal end vertical block may be pivotably mounted to the support arm distal end hub.

The intermediate beam may have a cavity, and the support arm may include at least one tension member that extends through the cavity of the intermediate beam and is secured at opposite ends to the support arm proximal end hub and the support arm distal end hub, the tension member securing the support arm proximal end hub, the support arm distal end hub, and the intermediate beam together.

According to another aspect of the invention, a support arm for supporting a payload includes a four bar linkage comprising lateral Links A and B, and upright Links X and Y at opposite ends of the lateral Links A and B; the Link Y being configured for pivotable movement about an axis P-P; a distal hub configured to support the payload for pivotable movement about an axis D-D; wherein the distal hub is mounted to the Link X for pivotable movement between a first position in which the axis D-D is at a first angle relative to the axis P-P and a second position in which the axis D-D is at a second angle relative to the axis P-P, wherein the first angle is different than the second angle.

Embodiments of the invention may include one or more of the following additional features separately or in combination.

The Link A may have a proximal end and a distal end, the proximal end of the Link A being pivotably mounted to the Link Y about a Link A proximal end pivot axis. The Link B may have a proximal end and a distal end, the proximal end of the Link B being pivotably mounted to the Link Y about a Link B proximal end pivot axis. The Link X may be pivotably mounted to the distal end of the Link A about a Link A distal end pivot axis and pivotably mounted to the distal end of the Link B about a Link B distal end pivot axis.

According to another aspect of the invention, a medical device support system includes a shaft; an extension arm mounted to the shaft for rotational movement about the shaft; and a load balancing arm including: a proximal hub mounted to the extension arm for pivotable movement about an axis P-P; a support arm having a proximal end and a distal end, the proximal end of the support arm being pivotably mounted to the proximal hub about a support arm proximal end pivot axis; a link having a proximal end and a distal end, the proximal end of the link being pivotably mounted to the proximal hub about a link proximal end pivot axis; a distal end vertical block pivotably mounted to the distal end of the support arm about a support arm distal end pivot axis and pivotably mounted to the distal end of the link about a link distal end pivot axis; and a distal hub configured to support a medical device load for pivotable movement about an axis D-D; wherein the distal hub is mounted to the distal end vertical block for pivotable movement between a first position in which the axis D-D is at a first angle relative to the axis P-P and a second position in which the axis D-D is at a second angle relative to the axis P-P, wherein the first angle is different than the second angle.

According to another aspect of the invention, there is provided a method of adjusting an angle of a distal hub of a load balancing arm relative to a proximal hub of the load balancing arm, including providing a load balancing arm having a proximal hub, a support arm, a link, and a distal end vertical block, wherein the proximal hub, the support arm, the link, and the distal end vertical block form a four bar linkage; wherein the proximal hub is configured for pivotable movement about an axis P-P; providing a distal hub configured to support a medical device load for pivotable movement about an axis D-D; and mounting the distal hub to the distal end vertical block for pivotable movement between a first position in which the axis D-D is at a first angle relative to the axis P-P and a second position in which the axis D-D is at a second angle relative to the axis P-P, wherein the first angle is different than the second angle.

Embodiments of the invention may include one or more of the following additional features separately or in combination.

The method may include mounting a medical device load to the distal hub for pivotable movement about the axis D-D.

The pivotably moving the distal hub may include moving a slot opening in the distal hub along a fastener projecting from the distal end vertical block into the slot opening.

The method may include threading the fastener into a threaded hole in the distal end vertical block until a head of the fastener engages the distal hub on opposite sides of the slot opening to secure the distal hub to the distal end vertical block.

The fastener may be a serrated flange screw and the threading may include tightening the serrated flange screw to a predetermined torque to displace some material in the distal hub to create a mechanical interference lock between a head of the serrated flange screw and the distal hub.

According to another aspect of the invention, a load balancing arm for a medical device support system includes a distal hub configured to support a medical device load for pivotable movement about an axis D-D; a support arm having a proximal end and a distal end, the distal end of the support arm being pivotably mounted to the distal hub about a support arm distal end pivot axis; a link having a proximal end and a distal end, the distal end of the link being pivotably mounted to the distal hub about a link distal end pivot axis; a proximal end vertical block pivotably mounted to the proximal end of the support arm about a support arm proximal end pivot axis and pivotably mounted to the proximal end of the link about a link proximal end pivot axis; and a proximal hub configured for pivotable movement about an axis P-P; wherein the proximal hub is mounted to the proximal end vertical block for pivotable movement between a first position in which the axis D-D is at a first angle relative to the axis P-P and a second position in which the axis D-D is at a second angle relative to the axis P-P, wherein the first angle is different than the second angle.

Embodiments of the invention may include one or more of the following additional features separately or in combination.

The proximal end vertical block may include a proximal end load adjustment base.

The proximal hub, the support arm, the link, and the proximal end vertical block may form a four bar linkage.

The proximal hub may be mounted to the proximal end vertical block for pivotable movement about the support arm proximal end pivot axis.

The support arm proximal end pivot axis and the link proximal end pivot axis may be substantially vertically aligned and the support arm distal end pivot axis and the link distal end pivot axis may be substantially vertically aligned.

The load balancing arm may be configured such that when the proximal hub is in the first position the axis D-D is not parallel to the axis P-P and when the proximal hub is in the second position the axis D-D is substantially parallel to the axis P-P.

The axis P-P may be a vertical axis P-P and the load balancing arm may be configurfed such that when the proximal hub is in the second position the axis D-D is a predetermined amount of degrees offset from the vertical axis P-P to compensate for assembly deflection resulting from the medical device load.

The proximal hub may include a slot opening and wherein the proximal end vertical block may have a fastener projecting therefrom that extends into the slot opening, and the proximal hub may be configured such that as the proximal hub is pivotably moved from the first position to the second position the slot opening moves along the fastener projecting therein.

Opposite ends of the slot opening may define maximum pivotable movement of the proximal hub relative to the proximal end vertical block.

The fastener may be a threaded fastener and the proximal end vertical block may have a threaded hole for threadingly receiving the fastener, and the fastener may have a head that is sufficiently wide to bridge the slot opening and that is configured when tightened to engage the proximal hub on opposite sides of the slot opening to secure the proximal hub to the proximal end vertical block.

The fastener may secure the proximal hub to the proximal end vertical block by means of friction provided by a clamp load of the fastener head exerted on the proximal hub.

The fastener may include a serrated flange screw and the size of the serrated flange screw and the materials of the serrated flange screw and proximal hub may be selected so that the serrated flange screw when tightened to a predetermined torque displaces some material in the proximal hub to create a mechanical interference lock between a head of the serrated flange screw and the proximal hub.

The support arm may include a support arm proximal end hub and a support arm distal end hub and an intermediate beam between the support arm proximal end hub and the support arm distal end hub, the support arm distal end hub being pivotably mounted to the distal hub, the proximal end vertical block being pivotably mounted to the support arm proximal end hub.

The intermediate beam may have a cavity, and the support arm may include at least one tension member that extends through the cavity of the intermediate beam and is secured at opposite ends to the support arm proximal end hub and the support arm distal end hub, the tension member securing the support arm proximal end hub, the support arm distal end hub, and the intermediate beam together.

According to another aspect of the invention, a support arm for supporting a payload includes a four bar linkage comprising lateral Links A and B, and upright Links X and Y at opposite ends of the lateral Links A and B; a proximal hub configured for pivotable movement about an axis P-P; the Link X being configured to support the payload for pivotable movement about an axis D-D; wherein the proximal hub is mounted to the Link Y for pivotable movement between a first position in which the axis D-D is at a first angle relative to the axis P-P and a second position in which the axis D-D is at a second angle relative to the axis P-P, wherein the first angle is different than the second angle.

Embodiments of the invention may include one or more of the following additional features separately or in combination.

The Link A may have a proximal end and a distal end, the proximal end of the Link A being pivotably mounted to the Link Y about a Link A proximal end pivot axis. The Link B may have a proximal end and a distal end, the proximal end of the Link B being pivotably mounted to the Link Y about a Link B proximal end pivot axis. The Link X may be pivotably mounted to the distal end of the Link A about a Link A distal end pivot axis and pivotably mounted to the distal end of the Link B about a Link B distal end pivot axis.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention.

FIG. 2 is an exploded isometric view of proximal and distal end outer hubs separated from the Links X, A, B, Y, of the load balancing arm shown in FIGS. 1A-1D.

FIG. 3A is an isolated isometric view of the distal end outer hub of the FIG. 2 load balancing arm, showing arc shape slot openings therein.

FIG. 3B is an enlarged isolated isometric view of a serrated fastener suitable for fastening the distal end outer hub to the Link X.

FIG. 4A is a side elevation view of the load balancing arm wherein the Link A length is equal to the Link B length, and showing the distal end vertical block Link X in hidden/dashed lines and fasteners installed in the arc shape slot openings of the distal end outer hub where the heads of the fasteners are omitted and the shanks of the fasteners are shown in cross section.

FIG. 4B is an enlarged view of the distal end of the FIG. 4A load balancing arm.

FIG. 5A is a side elevation view of a load balancing arm wherein the Link B length is relatively shorter than the Link A length, causing the Link X and distal end outer hub fastened thereto to angle inward, and showing the distal end vertical block Link X in hidden/dashed lines and fasteners installed in the arc shape slot openings of the distal end outer hub where the heads of the fasteners are omitted and the shanks of the fasteners are shown in cross section.

FIG. 5B is an enlarged view of the distal end of the FIG. 5A load balancing arm.

FIG. 6A is a side elevation view of the FIG. 5A load balancing arm wherein the distal end outer hub is adjusted clockwise, and showing the arc shape slot openings having been moved relative to the fasteners so that a bottom mounting surface of the distal end outer hub is parallel to horizontal and parallel to a top mounting surface of the proximal end hub.

FIG. 6B is an enlarged view of the distal end of the FIG. 6A load balancing arm.

FIG. 7 is a view similar to FIG. 6A except showing the load balancing arm rotated counterclockwise 40 degrees from the position shown in FIG. 6A.

FIG. 8 is a view similar to FIG. 6A except showing the load balancing arm rotated clockwise 40 degrees from the position shown in FIG. 6A.

FIG. 9A is a side elevation view of a load balancing arm wherein the Link A length is relatively shorter than the Link B length, causing the Link X and distal end outer hub fastened thereto to angle outward, and showing the distal end vertical block Link X in hidden/dashed lines and fasteners installed in the arc shape slot openings of the distal end outer hub where the heads of the fasteners are omitted and the shanks of the fasteners are shown in cross section.

FIG. 9B is an enlarged view of the distal end of the FIG. 9A load balancing arm.

FIG. 10A is a side elevation view of the FIG. 9A load balancing arm wherein the distal end outer hub is adjusted counterclockwise, and showing the arc shape slot openings having been moved relative to the fasteners so that a bottom mounting surface of the distal end outer hub is parallel to horizontal and parallel to a top mounting surface of the proximal end hub.

FIG. 10B is an enlarged view of the distal end of the FIG. 10A load balancing arm.

FIG. 11 is a view similar to FIG. 10A except showing the load balancing arm rotated counterclockwise 40 degrees from the position shown in FIG. 10A.

FIG. 15 is an exploded isometric view of proximal and distal end outer hubs separated from the Links X, A, B, Y, of a load balancing arm of a conventional medical device support system.

FIG. 16A is a side elevation view of a conventional load balancing arm wherein the Link A length is equal to the Link B length, and showing the distal end vertical block Link X in hidden/dashed lines.

FIG. 16B is an enlarged view of the distal end of the FIG. 16A load balancing arm.

FIG. 17A is a side elevation view of a conventional load balancing arm wherein the Link B length is relatively shorter than the Link A length, causing the Link X and distal end outer hub fastened thereto to angle inward, and showing the distal end vertical block Link X in hidden/dashed lines.

FIG. 17B is an enlarged view of the distal end of the FIG. 17A load balancing arm.

FIG. 19 is a view similar to FIG. 17A except showing the load balancing arm rotated clockwise 40 degrees from the position shown in FIG. 17A.

DETAILED DESCRIPTION

Figure 1A:
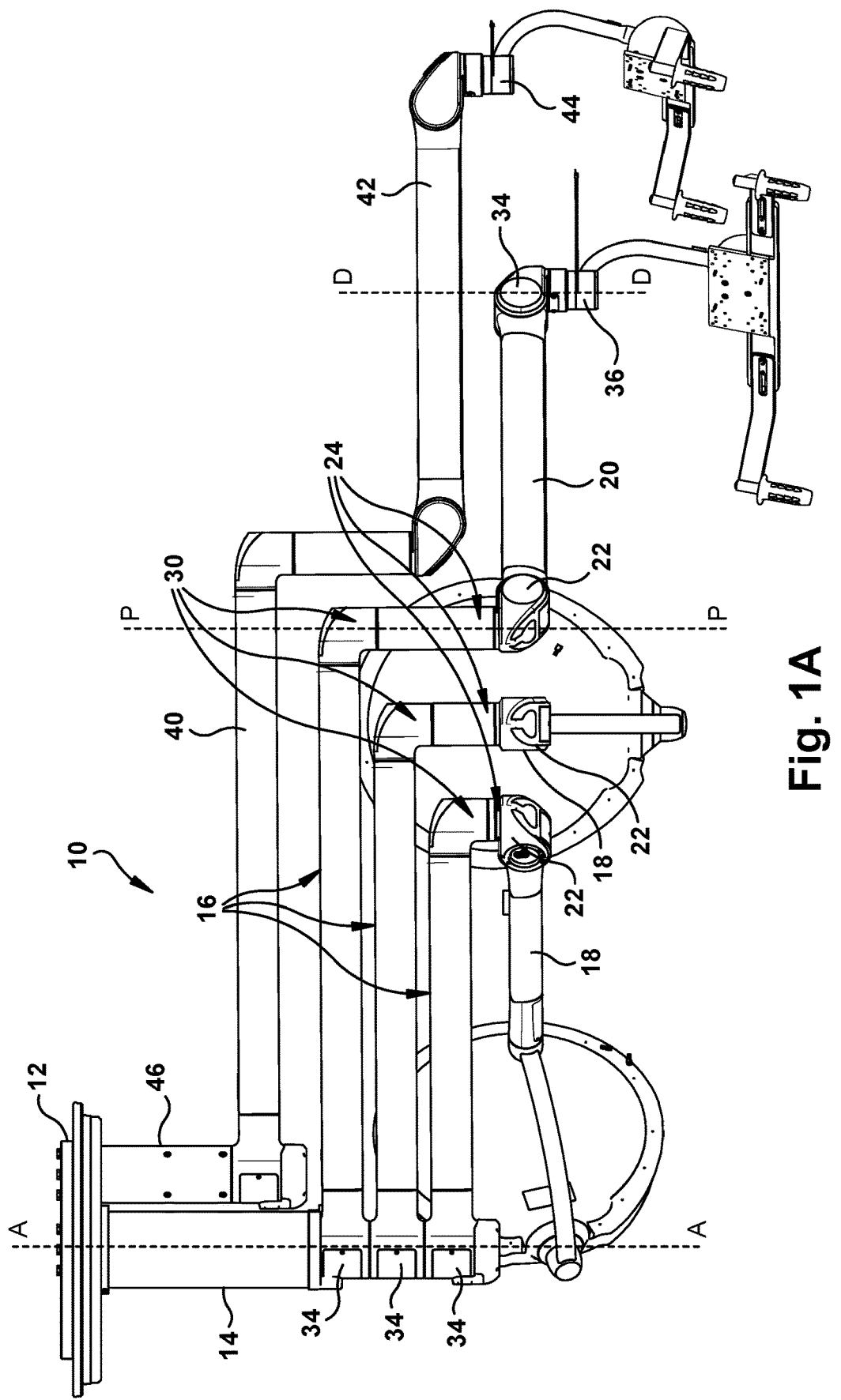
FIG. 1A is an isometric view of a medical device support system in accordance with an embodiment of the invention.

While the present invention can take many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications of the described embodiments, and any further applications of the principles of the invention as described herein, are contemplated as would normally occur to one skilled in the art to which the invention relates.

Referring again to FIGS. 15-20B, the inventors have found that the manufacturing tolerances of the components used to construct the four bar linkage combined with powder coating thickness variations within the stack up of tolerances may have the potential to cause the axis of the distal end of the load balancing arm 500 to go out of alignment, for example out of parallel, from the proximal end by plus or minus a certain amount of degrees calculated based on the maximum amount of tolerances stack up, for example, plus/minus (+/−) four degrees (4°). The inventors found that the largest dimensional variation in the load balancing arm 500 assembly comes from Link A, as Link A is constructed from the most components with the largest manufacturing tolerances. Link B has the second largest dimensional variation due to manufacturing tolerances. Due to relatively tight tolerances on the single component Links X and Y, Links X and Y have a relatively smaller impact in causing the out of parallel condition on the load balancing arm 500 assembly.

Figure 18:
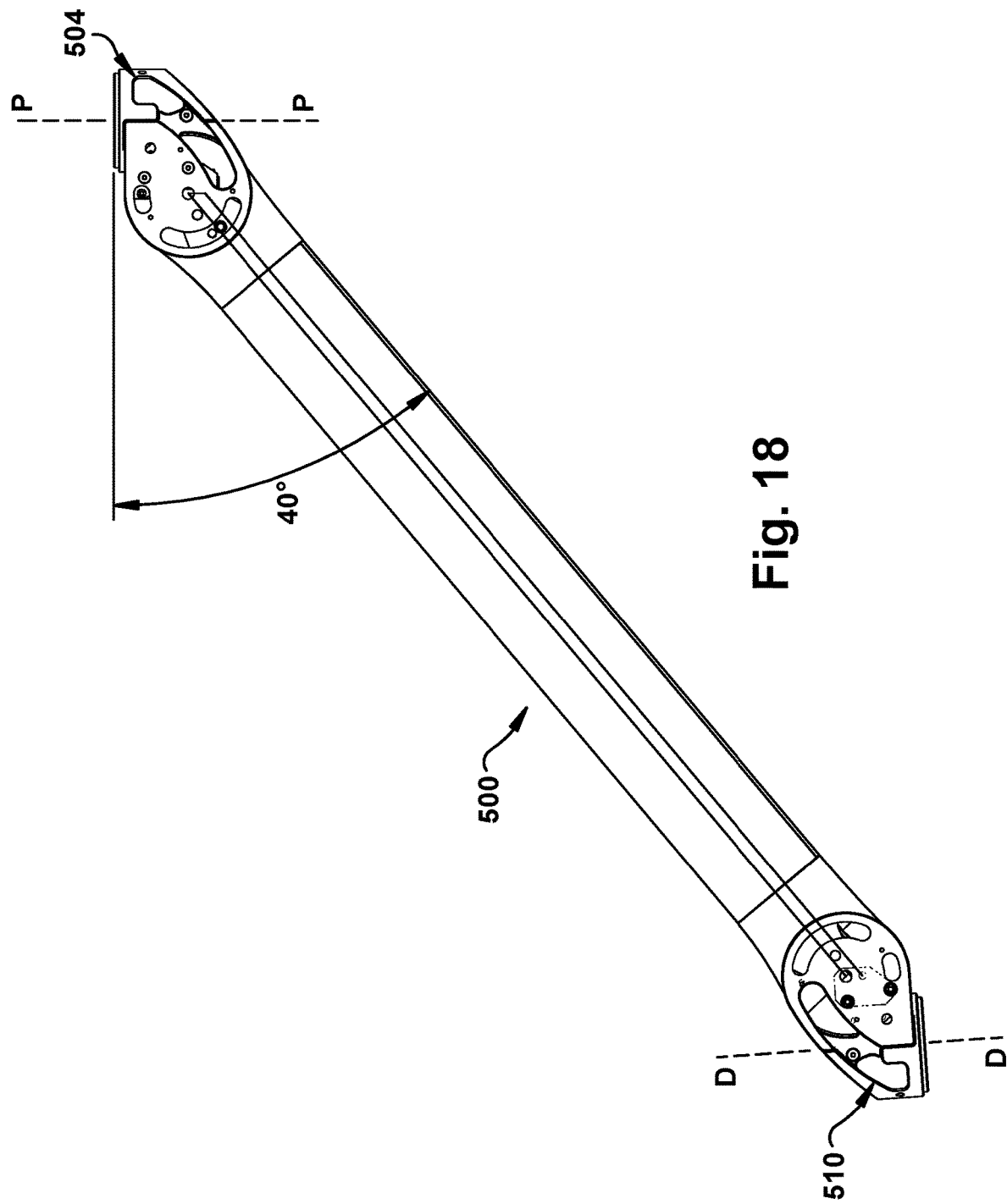
FIG. 18 is a view similar to FIG. 17A except showing the load balancing arm rotated counterclockwise 40 degrees from the position shown in FIG. 17A.
Figure 20A:
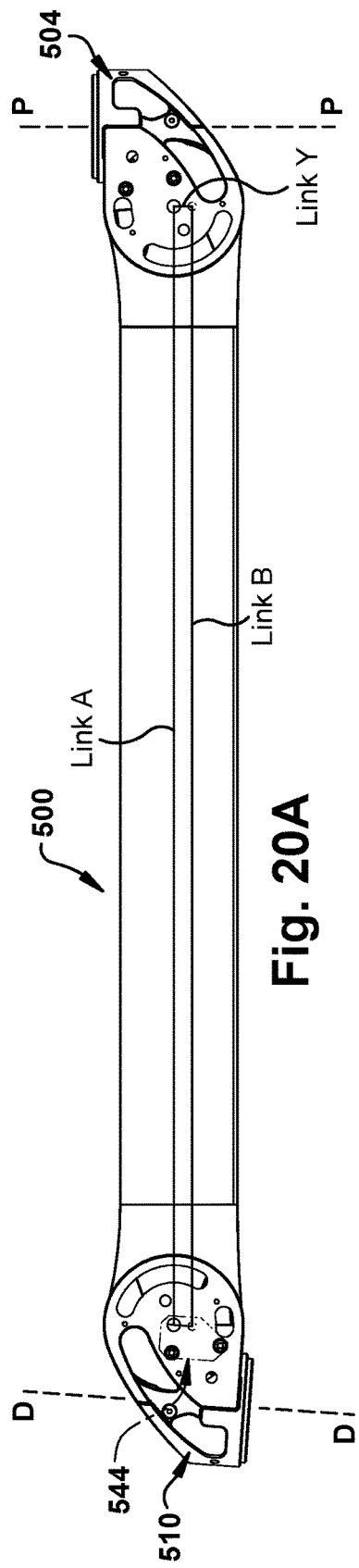
FIG. 20A is a side elevation view of a conventional load balancing arm wherein the Link A length is relatively shorter than the Link B length, causing the Link X and distal end outer hub fastened thereto to angle outward, and showing the distal end vertical block Link X in hidden/dashed lines.
Figure 20B:
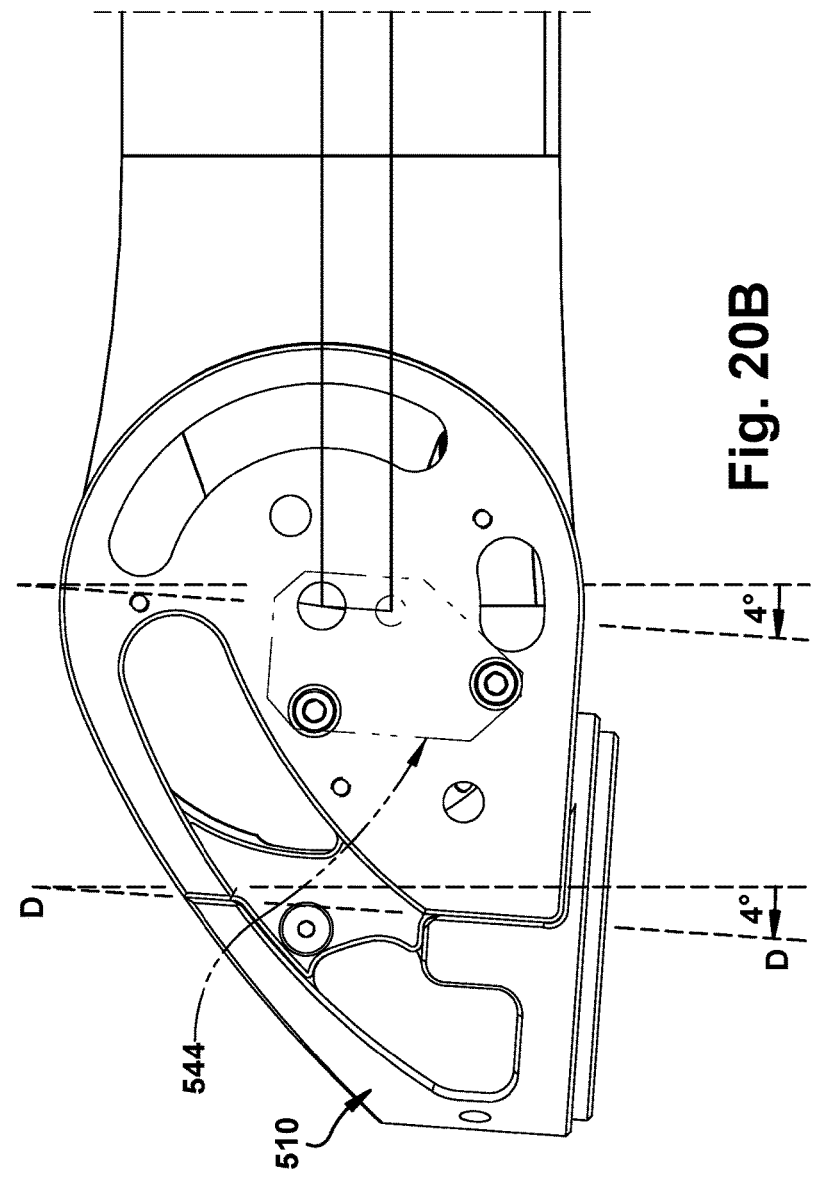
FIG. 20B is an enlarged view of the distal end of the FIG. 20A load balancing arm.

The inventors have found that the main cause of an out of parallel condition is a length differential between Link A and Link B. FIGS. 16A-20B are illustrative. FIGS. 16A-16B show the load balancing arm 500 wherein Link A and Link B are equal in length, resulting in little or no out of parallel condition. Thus, the axis D-D defined by the distal end outer hub 510 and about which a medical device load pivots when pivotably mounted to the distal end outer hub 510 is parallel to the axis P-P of the proximal end outer hub 504. FIGS. 17A-17B show the load balancing arm 500 wherein the Link B length is relatively shorter than the Link A length. This causes the Link X and consequently the distal end vertical block 544 and distal end outer hub 510 fastened to the vertical block 544, to angle inward; that is, the Link X and the Link Y are out of parallel, as shown about four degrees (4°) inward. As a consequence, the axis D-D defined by the distal end outer hub 510 is out of alignment, or out of parallel, relative to the axis P-P of the proximal end outer hub 504. As shown in FIGS. 18 and 19, this out of parallel condition remains with the load balancing arm 500 even when the load balancing arm 500 is rotated counterclockwise 40 degrees from the position shown in FIG. 17A, or rotated clockwise 40 degrees from the position shown in FIG. 17A, respectively. FIGS. 20A and 20B show the load balancing arm 500 wherein the Link A length is relatively shorter than the Link B length. This causes the Link X and consequently the distal end vertical block 544 and the distal end outer hub 510 fastened to the vertical block 544, to angle outward; that is, the Link X and the Link Y are out of parallel, as shown about four degrees (4°) outward. As a consequence, here too the axis D-D defined by the distal end outer hub 510 is out of alignment, or out of parallel, relative to the axis P-P of the proximal end outer hub 504. Thus, when Link B is shorter than Link A, the distal end (Link X) angles inward and when Link B is longer than Link A the opposite effect occurs.

The proximal end of the load balancing arm 500 may be considered to be mounted level to horizontal or level to the extension arm. Based on this consideration the angular variability manifests itself at the distal end of the load balancing arm 500; that is, the angular variability is not split between the distal end and the proximal end of the load balancing arm 500. By way of example, if the differential length between Link A and Link B is at the highest end of the tolerance stack up, the distal end outer hub 510 of the load balancing arm 500 will be a maximum amount of degrees outward, for example four degrees (4°) outward, and the proximal end outer hub 504 will still be zero degrees (0°) rather than, for example, the proximal end outer hub 504 and the distal end outer hub 510 each being half the maximum amount of degrees, or two degrees (2°), out of alignment. The tolerance data for each Link X and Link Y can be used to calculate a maximum outward angle and a maximum inward angle at the distal end outer hub 510 of the load balancing arm 500 based on tolerance stack ups. For example, FIGS. 17A-17B show an example of a maximum outward angle, which in FIGS. 17A-17B is about four degrees (4°). FIGS. 20A-20B show an example of a maximum inward angle, which is about four degrees (4°).

The inventors created a parallelism adjustment mechanism to improve the accuracy in alignment of the components of the load balancing arm 500, for example to remove an out of parallel condition caused by the stack up of manufacturing tolerances in the components. As will be described in greater detail below, the invention relates to a parallelism adjustment mechanism 200 for a load balancing arm 20 of a medical device support system 10, wherein the parallelism adjustment mechanism 200 ensures the vertical axes D-D, P-P of the distal end and proximal end outer hubs of the load balancing arm 20 are aligned, for example parallel.

Turning then to FIG. 1A, there is shown a medical device support system 10 in accordance with an embodiment of the invention. The medical device support system 10 includes a vertically oriented shaft or support column 14 that is suspended from a ceiling support 12, and three generally horizontal extension arms 16 mounted to the shaft 14 for rotational movement about an axis A-A of the shaft 14. The shaft 14 could be mounted to a wall or stand rather than the ceiling. Three load balancing arms, two at reference numeral 18 and one at reference numeral 20, which are also referred to as counterbalancing arms or spring arms, are mounted to the respective extension arms 16. In the FIG. 1A embodiment, a proximal hub 22 of the load balancing arm 18, 20 includes a support structure 24, which may include a drop tube, that is rotatably connectable to a receptacle at the distal end 30 of the extension arm 16 for rotation about the axis P-P. The distal end of the right most illustrated load balancing arm 20 is configured with a distal hub 34 that rotatably supports a medical device 36 about the axis D-D. The medical device 36 may include a patient monitor as shown, or a surgical light (shown on load balancing arms 18 but with a different type of distal end hub), a supply console, a camera detector head, a medical instrument, a ventilator system, a suction device, among others. A control console, if provided, may provide controls for navigation of a medical instrument that is either coupled to or remote from the load balancing arm 18. The load balancing arm 18 enables positioning of the medical device 36 to a proper orientation relative to for example a patient operating table and healthcare professionals in the operating room. An additional extension arm 40, support arm 42, and medical device 44 may be pivotably mounted to a separate vertically oriented shaft 46 radially offset from the shaft 14.

FIGS. 1B, 1C, 2 and 3A-3B show an example of a load balancing arm 20 in accordance with an embodiment of the invention. The load balancing arm 20 may include a four bar, four pin joint linkage construction. The four bar linkage is formed by lateral Links A and B, and upright Links X and Y at opposite ends of the lateral Links A and B.

Link A is a support arm 50 and may be constructed of an intermediate beam 52, and a proximal end inner hub 56 of the proximal hub 22 and a distal end inner hub 58 of the distal hub 34 at opposite ends of the intermediate beam 52, where the Link A extends between pivot pins 60 and pivot pins 62. A powder coating layer may be provided on the proximal end inner hub 56 and distal end inner hub 58. A cavity 70 extends longitudinally through the intermediate beam 52 the entire length of the intermediate beam 52. At least one tension member, for example a tie rod, four such tension members 80 (only three in view in FIG. 1B, and two in view in FIG. 1C) in the illustrative embodiment, extend through the cavity 70 of the intermediate beam 52. The tension members 80 are secured at their proximal ends to the proximal end inner hub 56 and at their distal ends to the distal end inner hub 58. The tension members 80-86 are in a state of tension and the intermediate beam 52 is in a state of compression. Thus, the intermediate beam 52 can be said to be "sandwiched" between the proximal end inner hub 56 and distal end inner hub 58.

Additional detail of an exemplary load balancing arm incorporating tension members is shown in U.S. patent application Ser. No. 16/702,932, filed on Dec. 4, 2019, and published as U.S. Patent Application Publication Number 2020/0246109, which is incorporated herein by reference.

Link B may be constructed as a parallel link assembly 90 between a pivot pin 92 and a pivot pin 94. As shown in FIGS. 1D and 2, the illustrative parallel link assembly 90 is a U-shape link having two vertically oriented laterally spaced parallel side walls 102 and a lower bridge member 104 connecting the bottom edges of the side walls 102. It will be appreciated that the parallel link assembly 90 may comprise two parallel links in the form of the two parallel side walls 102 with the lower bridge member 104 omitted, or even a single link. In the present embodiment, the parallel link assembly 90 is made up of three pieces comprising a U-shape stainless steel member 106 and a pair of relatively harder stainless steel side braces 108 spot welded to the U-shape stainless steel member 106.

Link X may be in the form of a distal end vertical block 112 between the pivot pin 94 and the pins 60. In the illustrative embodiment, the pin 94 is vertically aligned with respect to the pins 60.

Link Y may be made up of a load adjustment base 114 between the pins 62 and the pin 92. In the illustrative embodiment, the pin 92 is vertically aligned with respect to the pins 62.

The proximal hub 22 of the load balancing arm 20 also includes a proximal end outer hub 120, and the distal hub 34 includes a distal end outer hub 122. As shown in FIG. 4A, the proximal end outer hub 120 may be fastened to the load adjustment base 114 by means of fasteners 136, 138. More specifically, as shown in FIGS. 2 and 4A, the fasteners 136, 138 are inserted through through-holes 146, 148 in vertically oriented opposite side walls 156 of the proximal end outer hub 120 and threaded into threaded holes 166, 168 in opposite side walls of the load adjustment base 114.

The distal end outer hub 122 may be fastened to the distal end vertical block 112 by means of fasteners 176, 178. FIGS. 3A-3B show greater detail of the distal end outer hub 122 and an exemplary fastener. Unlike the distal end outer hub 510 of the load balancing arm 500 shown in FIGS. 15-20B, which has through-hole openings 642, 644, the distal end outer hub 122 according to the present embodiment has slot openings 196, 198, arc shape slot openings in the illustrated embodiment, that enable the distal end outer hub 122 to be pivotably adjusted about the pivot pins 60 and pivotably adjusted relative to the distal end vertical block 112. The fasteners 176, 178 and the arc shape slot openings 196, 198 form the parallelism adjustment mechanism 200 of the load balancing arm 20, the details of which are described in greater detail below. As shown in FIGS. 2, 3A-3B, and 4A-4B, the fasteners 176, 178 are inserted through the arc shape slot openings 196, 198 in vertically oriented opposite side walls 202 of the distal end outer hub 122 and threaded into threaded holes 206, 208 in opposite side walls of the distal end vertical block 112.

Figure 1B:
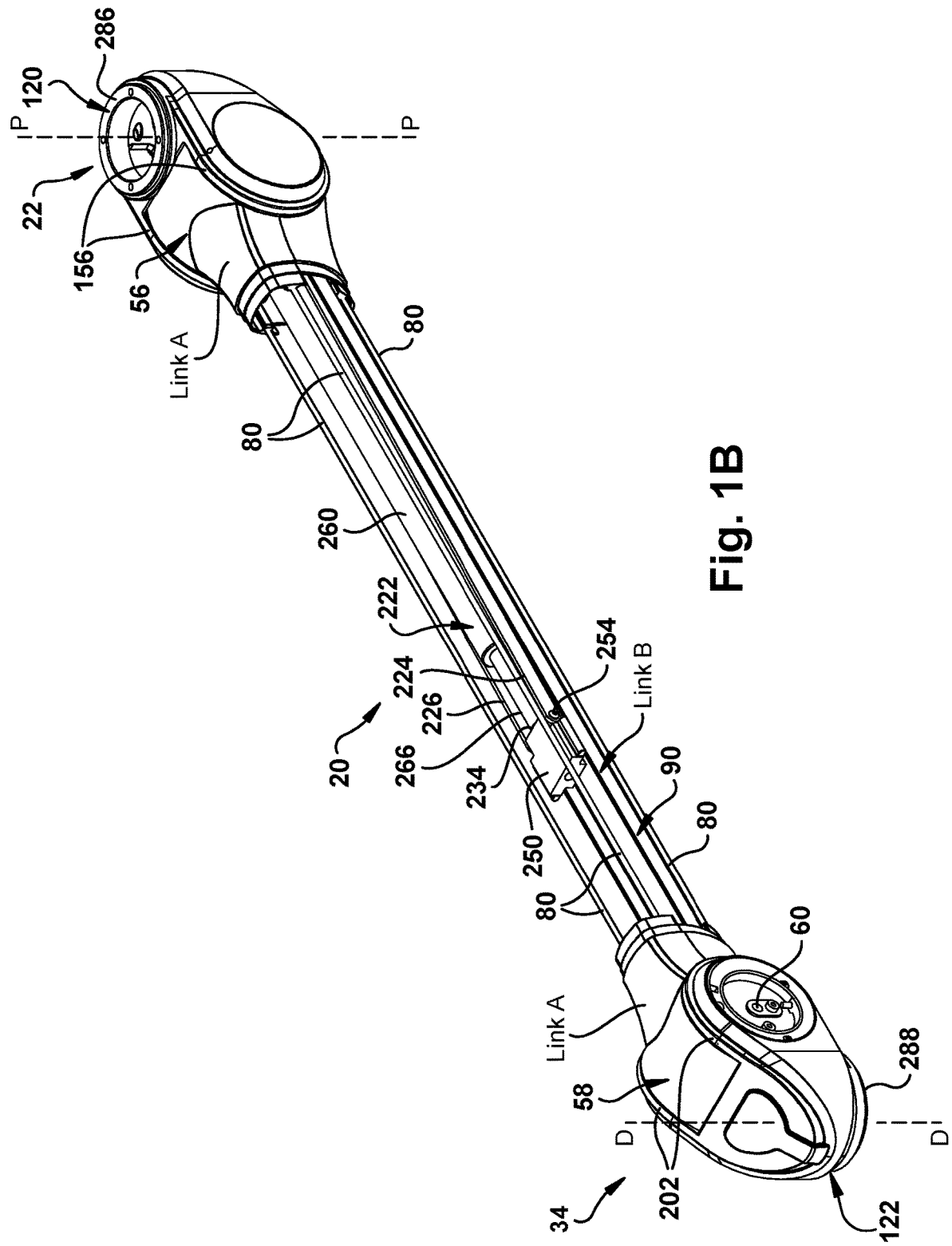
FIG. 1B is top isometric view of a load balancing arm of the FIG. 1A medical device support system in accordance with an embodiment of the invention, with a support arm structure removed to show internal components of the load balancing arm.
Figure 1C:
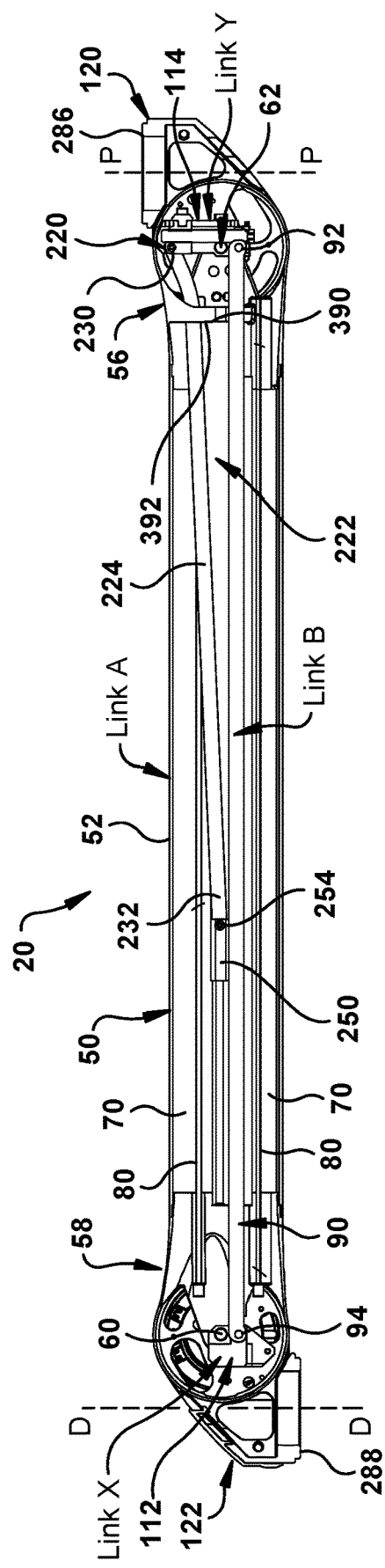
FIG. 1C is a side cross section view of the FIG. 1B load balancing arm in a substantially horizontal position, showing internal components of the load balancing arm.
Figure 1D:
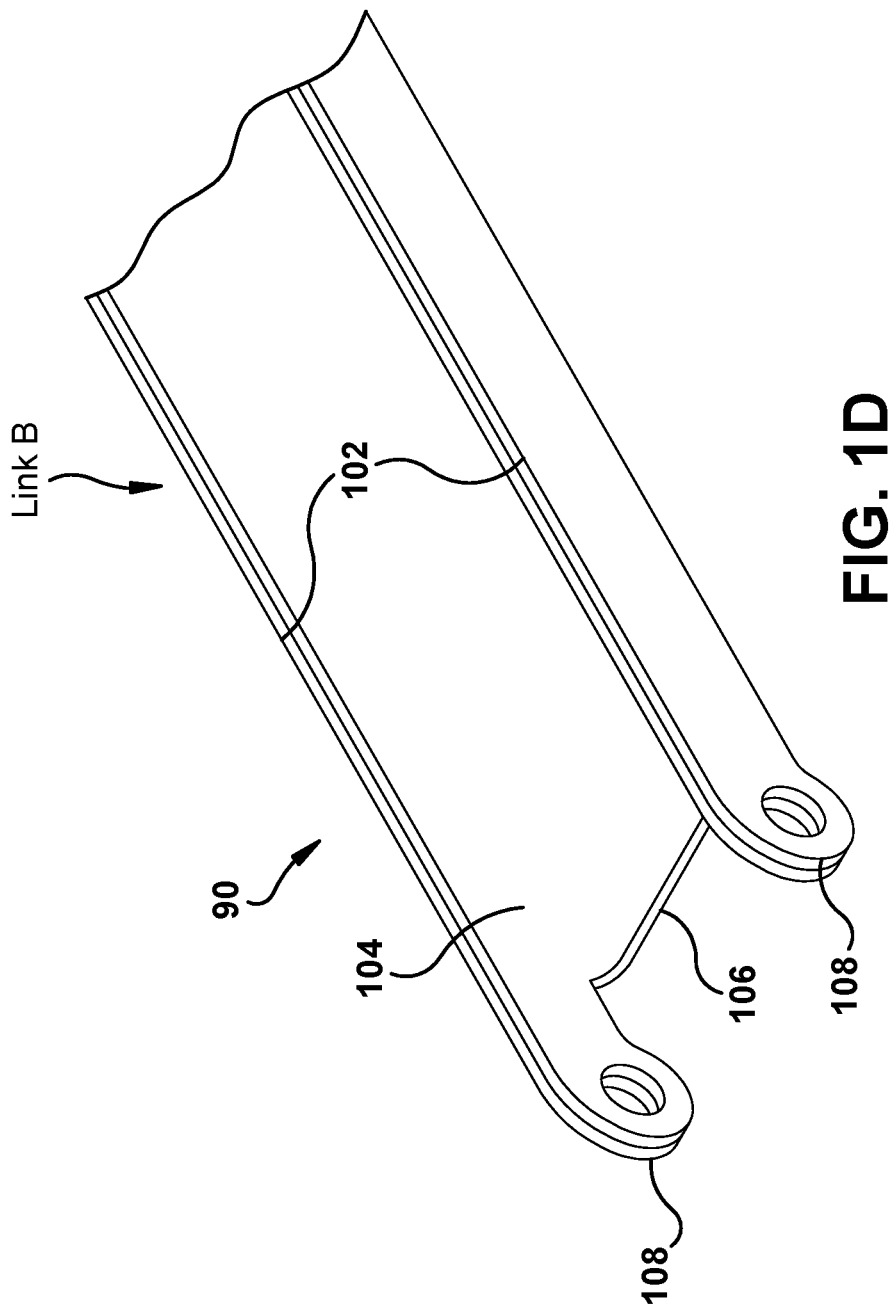
FIG. 1D is an isometric view of an end portion of a parallel link assembly of the FIG. 1B load balancing arm.

Referring to FIGS. 1B and 1C, the load balancing arm 20 may also include an adjustable bearing element 220, a spring 222, and one or more links, two such links 224, 226 in the illustrative embodiment. The spring 222 provides the balancing force via the links 224, 226 that balances the medical device load 36 at the distal end of the load balancing arm 20. The adjustable bearing element 220 includes an adjustable pivot pin 230 that is adjustable vertically relative to the pivot pins 62. The proximal end inner hub 56 is pivotably mounted to the pivot pins 62, which enables pivotable movement of the load balancing arm 20 about the pivot pins 62. Pivotable movement of the load balancing arm 20 about the main pivot axis defined by the pivot pins 62 raises and lowers the height of the medical device load 36 at the distal end of the load balancing arm 20. As will be appreciated, the distance between the adjustable pivot pin 230 and the main pivot axis defined by the pins 62 provides the mechanical advantage, or moment, that allows the load balancing arm 20 to balance the medical device load 36 at the distal end of the arm 20. The counterbalancing moment, and thus the balancing force, can be adjusted by adjusting the height of the pin 230 relative to the pivot pins 62 by means of the adjustable bearing element 220.

Distal ends 232 of the links 224, 226 are pivotably mounted to a distal end 234 of the spring 222 via a carriage slide 250 that is slidable relative to the structure that forms the support arm 50. The pivotable connection may be facilitated by, for example, a pin 254 mounted within the carriage slide 250. The spring 222 may be any type of counterbalancing member, and in the illustrative embodiment is a compression gas spring 222. The spring 222 is oriented along an axis that extends radially from and perpendicular to the main pivot axis defined by the pivot pins 62. The spring 222 has a cylinder 260 and a rod 262. The cylinder 260 has a proximal end wall 270 that is coupled to a vertical beam 272 of the support arm 50. The vertical beam 272 is sufficiently narrow that the links 224, 226 straddle the vertical beam 272 on opposite lateral sides thereof throughout the pivotable range of the load balancing arm 20. The rod 262 is pivotably mounted to the distal ends 232 of the links 224, 226 via the pin 254 of the afore described carriage slide 250. In operation, the links 224, 226 straddle the spring 222 on laterally opposite sides of the spring 222 throughout the pivotable range of the load balancing arm 20.

Additional detail of an exemplary load balancing arm incorporating an adjustable bearing element, a spring, and links is shown in U.S. patent application Ser. No. 16/703,000, filed on Dec. 4, 2019, and published as U.S. Patent Application Publication Number 2020/0246110, which is incorporated herein by reference.

The proximal end outer hub 120 is coupled to the support structure 24, for example drop tube, which in turn is pivotably mounted about an axis P-P to the distal end 30 of the extension arm 16. In the illustrative embodiment, the axis P-P is a vertical axis and is parallel to the vertical axis A-A of the shaft 14. The proximal end outer hub 120 may include a mounting surface 286 for mounting the proximal end outer hub 120 and thus the load balancing arm 20 to, for example, the support structure 24 at the distal end of the extension arm 16. The axis P-P desirably is parallel to the vertically aligned pins 62, 92 of the load adjustment base 114. The medical device load 36 such as a patient monitor or the like is pivotably mounted about the axis D-D to the distal end outer hub 122. The distal end outer hub 122 may include a mounting surface 288 for mounting the medical device load 36 thereto and thus to the distal end of the load balancing arm 20. The axis D-D desirably is parallel to the vertically aligned pins 60, 94 of the distal end vertical block 112. The mounting surface 288 desirably is parallel to the mounting surface 286. The support arm 50 is pivotable at its proximal end inner hub 56 about a main pivot axis defined by the centers of the pivot pins 62 of the load adjustment base 114. The support arm 50 is pivotable at its distal end inner hub 58 about a pivot axis defined by the centers of the pivot pins 60 of the distal end vertical block 112. The parallel link assembly 90 is pivotable at its proximal end about a pivot axis defined by the centers of the pivot pins 92, and pivotable at its distal end about a pivot axis defined by the centers of the pivot pins 94.

In the four bar linkage of the above load balancing arm 20, it is desirable that the Link A and Link B lengths are equal and that the Link X and Link Y lengths are equal. In this way, the vertically aligned pins 60, 94 and the axis D-D of the distal end outer hub 122 remain parallel to the vertically aligned pins 62, 92 and the axis P-P of the proximal end outer hub 120 throughout the pivotable range of the load balancing arm 20 about the main pivot axis defined by the pivot pins 62. However, as described above with respect to FIGS. 15-20B, owing to the stack up of manufacturing tolerances in the components that form the load balancing arm 20, the Link A and Link B lengths may not always be equal and the Link X and Link Y lengths may not always be equal, causing an out of alignment, for example out of parallel, condition between the axis D-D and the axis P-P.

The parallelism adjustment mechanism 200 including the fasteners 176, 178 and the arc shape slot openings 196, 198 enables the axis D-D to be angularly adjusted relative to the axis P-P to compensate for such out of alignment caused by the stack up of manufacturing tolerances.

With reference to FIGS. 3A-3B and 4A-4B, greater detail of the parallelism adjustment mechanism 200 will now be described. As shown in FIGS. 4A-4B, the fasteners 176, 178 and the arc shape slot openings 196, 198 are positioned at first and second radial distances R1, R2, respectively, from the centers of the pivot pins 60 about which the distal end vertical block 112 is pivotably mounted. The arcs of the arc shape slot openings 196, 198 are defined by the respective first and second radial distances R1, R2. In FIGS. 4A-4B, the fasteners 176, 178 are shown in the center of the respective arc shape slot openings 196, 198. As the distal end outer hub 122 is pivoted about the pivot pins 60, the arc shape slot openings 196, 198 move along the respective fasteners 176, 178 projecting therein from the distal end vertical block 112. Opposite ends of the arc shape slot openings 196, 198 define the maximum pivotable movement of the distal end outer hub 122 relative to the distal end vertical block 112, which in the illustrative embodiment is based on the maximum of the stack up of manufacturing tolerances in the components that make up the load balancing arm 20. In the illustrative embodiment, the arc shape slot openings 196, 198 are sized and the fasteners 176, 178 are selected to allow the distal end outer hub 122 to be pivoted approximately four degrees (4°) clockwise and approximately four degrees (4°) counterclockwise about the pivot pins 60 from the centers of the respective arc shape slot openings 196, 198; thus, the total angular displacement range of the distal end outer hub 122 relative to the distal end vertical block 112 and about pivot pins 60 is about eight degrees (8°). As will be appreciated, because the second radial distance R2 is greater than the first radial distance R1, the corresponding arcuate span of the arc shape slot opening 198 is larger than that of the arc shape slot opening 196.

FIGS. 4A-4B show the fasteners 176, 178 installed in the arc shape slot openings 196, 198 of the distal end outer hub 122 where for ease of reference and clarity purposes the heads of the fasteners 176, 178 are omitted and the shanks of the fasteners 176, 178 are shown in cross section. The shank diameters of the fasteners 176, 178 are slightly less than the width of the respective openings 196, 198 in the radial direction. As shown in FIG. 3B, the heads of the fasteners 176, 178 are sufficiently wide to bridge the respective arc shape slot openings 196, 198. As such, when the fasteners 176, 178 are tightened, the fasteners 176, 178 engage the distal end outer hub 122 on opposite sides of the arc shape slot openings 196, 198 to secure the distal end outer hub 122 to the distal end vertical block 112. Also as shown in FIG. 3B, the fasteners 176, 178 may be serrated flange screws. The size of the serrated flange screws 176, 178 and the materials of the serrated flange screws 176, 178 and distal end outer hub 122 may be selected so that the serrated flange screws 176, 178, when tightened to a predetermined torque, displace some material in the distal end outer hub 122 to create a mechanical interference lock between heads of the serrated flange screws 176, 178 and the distal end outer hub 122. Other types of fasteners may also be suitable for the parallelism adjustment mechanism 200, for example, socket head cap screws or shoulder screws. In some embodiments, the fasteners 176, 178 may secure the distal end outer hub 122 to the distal end vertical block 112 merely by means of friction provided by a clamp load of the heads of the fasteners 176, 178 exerted on the distal end outer hub 112.

FIGS. 4A-12 illustrate the manner by which the parallelism adjustment mechanism 200 compensates for an out of parallel condition between the axis D-D and the axis P-P. FIGS. 4A-4B show the load balancing arm 20 wherein Link A and Link B are equal in length, resulting in little or no out of parallel condition. As shown in FIG. 4B, the threaded fasteners 176, 178 reside in the centers of the arcuate spans of the respective arc shape slot openings 196, 198. In FIGS. 4A-4B, the axis D-D defined by the distal end outer hub 122 and about which a medical device load 36 pivots when pivotably mounted to the distal end outer hub 122 is parallel to the axis P-P of the proximal end outer hub 120. Consequently, the parallelism adjustment mechanism 200 is not used to adjust the axis D-D relative to the axis P-P.

FIGS. 5A-5B show the load balancing arm 20 wherein the Link B length is relatively shorter than the Link A length. This causes the Link X and consequently the distal end vertical block 112 and distal end outer hub 122 fastened to the vertical block 122, to angle inward; that is, the Link X and the Link Y are out of parallel, in the illustrative embodiment about four degrees (4°) inward. To compensate for this out of parallel condition, the distal end outer hub 122, with the fasteners 176, 178 loosened, may be pivoted four degrees (4°) clockwise about the pivot pins 60 and relative to the distal end vertical block 112 from the position shown in FIGS. 5A-5B to the position shown in FIGS.

6A-6B. As shown in FIGS. 6A-6B, ends of the arc shape slot openings 196, 198 abut the shanks of the fasteners 176, 178, indicating that the out of parallel condition exhibited by the Link X and Link Y is at a maximum of the stack up of manufacturing tolerances in the components that make up the load balancing arm 20.

The adjustment by the parallelism adjustment mechanism 200 brings the axis D-D defined by the distal end outer hub 122 into alignment, or parallel, relative to the axis P-P of the proximal end outer hub 120. As shown in FIG. 6A, this angular adjustment of the distal end outer hub 122 relative to the distal end vertical block 112 also adjusts the mounting surface 288 of the distal end outer hub 122 to be level to horizontal or level to the mounting surface 286 of the proximal end outer hub 120 and, consequently, level to the extension arm 13. The fasteners 176, 178 can then be tightened at the desired adjustment to secure the distal end outer hub 122 to the distal end vertical block 112. As shown in FIGS. 7 and 8, the adjusted parallel condition remains with the load balancing arm 20 even when the load balancing arm 20 is rotated counterclockwise 40 degrees from the position shown in FIG. 5A, or rotated clockwise 40 degrees from the position shown in FIG. 5A, respectively.

FIGS. 9A-9B show the load balancing arm 20 wherein the Link A length is relatively shorter than the Link B length. This causes the Link X and consequently the distal end vertical block 112 and distal end outer hub 122 fastened to the vertical block 122, to angle outward; that is, the Link X and the Link Y are out of parallel, in the illustrative embodiment about four degrees (4°) outward. To compensate for this out of parallel condition, the distal end outer hub 122, with the fasteners 176, 178 loosened, may be pivoted four degrees (4°) counterclockwise about the pivot pins 60 and relative to the distal end vertical block 112 from the position shown in FIGS. 9A-9B to the position shown in FIGS. 10A-10B. As shown in FIGS. 10A-10B, ends of the arc shape slot openings 196, 198 abut the shanks of the fasteners 176, 178, indicating that the out of parallel condition exhibited by the Link X and Link Y is at a maximum of the stack up of manufacturing tolerances in the components that make up the load balancing arm 20.

Figure 12:
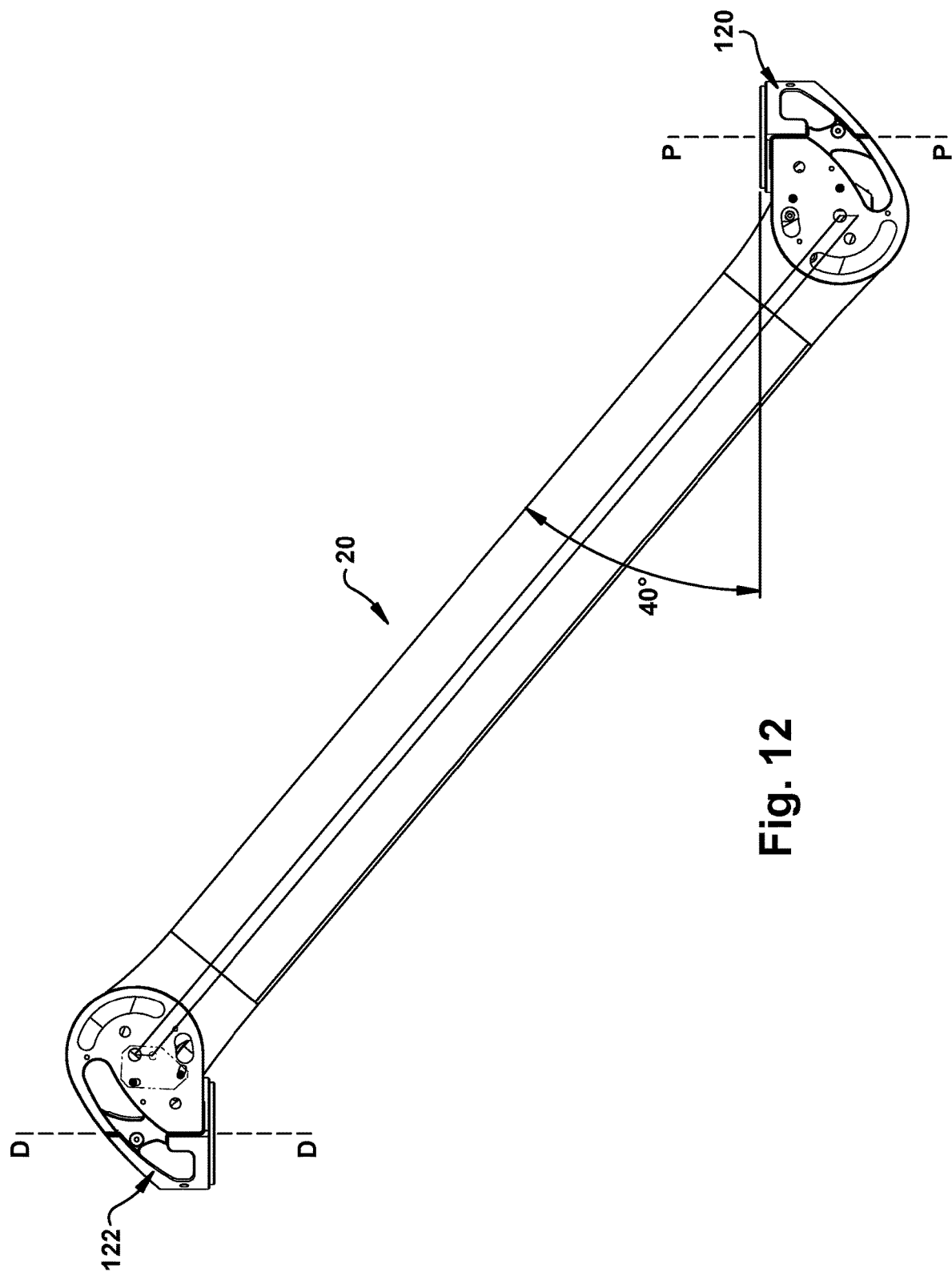
FIG. 12 is a view similar to FIG. 10A except showing the load balancing arm rotated clockwise 40 degrees from the position shown in FIG. 10A.

The adjustment by the parallelism adjustment mechanism 200 brings the axis D-D defined by the distal end outer hub 122 into alignment, or parallel, relative to the pivot axis P-P of the proximal end outer hub 120. As shown in FIG. 10A, this angular adjustment of the distal end outer hub 122 relative to the distal end vertical block 112 also adjusts the mounting surface 288 of the distal end outer hub 122 to be level to horizontal or level to the mounting surface 286 of the proximal end outer hub 120 and, consequently, level to the extension arm 13. The fasteners 176, 178 can then be tightened at the desired adjustment to secure the distal end outer hub 122 to the distal end vertical block 112. As shown in FIGS. 11 and 12, the adjusted parallel condition remains with the load balancing arm 20 even when the load balancing arm 20 is rotated counterclockwise 40 degrees from the position shown in FIG. 9A, or rotated clockwise 40 degrees from the position shown in FIG. 9A, respectively.

It will be appreciated that the parallelism adjustment mechanism 200 may not necessarily adjust the pivot axes D-D and P-P to be parallel or to adjust the mounting surface 288 to be level to horizontal or level to the mounting surface 286. Other embodiments are contemplated. For example, the distal end outer hub 122 may be pivotably adjusted relative to the distal end vertical block 112 up to a predetermined amount of degrees of upward bias, for example one degree (1°) upward bias, to compensate for assembly deflection resulting from the medical device load 36 being assembled to the distal end outer hub 122. Thus, initially the distal end outer hub 122 is mounted to the distal end vertical block 112 where the axis D-D is at a first angle relative to the axis P-P. At the first angle, the axis D-D may be parallel to or not parallel to the axis P-P. The distal end outer hub 122 is then pivoted about the pivot pins 60 so that the axis D-D is at a second angle relative to the axis P-P. At the second angle, the axis D-D is positioned to provide a one degree (1°) upward bias to compensate for assembly deflection, that is, the axis D-D is one degree offset from the axis P-P (not parallel to the axis P-P), or one degree (1°) offset from vertical, and the mounting surface 288 is one degree (1°) upward relative to horizontal or relative to the mounting surface 286. The distal end outer hub 122 is then locked in this one degree (1°) upward bias position by tightening the fasteners 176, 178 to secure the distal end outer hub 122 to the distal end vertical block 112. The medical device load 36, for example patient monitor, is then assembled to the distal end outer hub 122. The weight of the medical device load 36 deflects the load balancing arm 20 downward about one degree (1°), rendering the axis D-D parallel to the axis P-P, and the mounting surface 288 parallel to the mounting surface 286.

The above described parallelism adjustment mechanism 200 has a pair of arc shape slot openings 196, 198 in the vertically oriented opposite side walls 202 of the distal end outer hub 122, a pair of threaded openings 206, 208 in opposite side walls of the distal end vertical block 112, and fasteners 176, 178 that pass through the arc shape slot openings 196, 198 and thread into the threaded openings 206, 208, thereby to secure the distal end outer hub 122 to the distal end vertical block 112. The illustrative parallelism adjustment mechanism 200 thus has four fasteners, four arc shape slot openings, and four threaded openings. The parallelism adjustment mechanism 200 need not be limited as such, and other embodiments are contemplated. In some embodiments, there may be one arc shape slot opening in one of the vertically orientated side walls 202 of the distal end outer hub 122, one threaded opening in a correspond one of the opposite side walls of the distal end vertical block 112, and one fastener that passes through the one arc shape slot opening and threads into the one threaded opening.

In the illustrative embodiment, the slot openings 196, 198 are arc shape slot openings 196, 198 positioned at first and second radial distances R1, R2, respectively, from the centers of the pivot pins 60 about which the distal end vertical block 112 is pivotably mounted. As will be appreciated, the slot openings 196, 198 need not be arc shape and other embodiments are contemplated. For example, the slot openings 196, 198 may instead have a rectangular shape so long as when the distal end outer hub 122 is pivoted about the pivot pins 60, the slot openings 196, 198 move along the respective fasteners 176, 178 projecting therein from the distal end vertical block 112 over the angular displacement range of the distal end outer hub 122, and so long as the fasteners 176, 178 when tightened engage the distal end outer hub 122 on opposite sides of the slot openings 196, 198 to secure the distal end outer hub 122 to the distal end vertical block 112.

In the above described load balancing arm 20, the parallelism adjustment mechanism 200 pivotably adjusts the distal end outer hub 122 relative to the distal end vertical block 112 and, once the distal end outer hub 122 is secured to the distal end vertical block 112, the distal end outer hub 122 together with the distal end vertical block 112 are pivotable about the pivot pins 60 relative to the distal end inner hub 58 of the support arm 50. As used herein the term "outer" in distal end outer hub 122 and proximal end outer hub 120, and the term "inner" in distal end inner hub 58 and proximal end inner hub 56, are used to facilitate understanding of the illustrative embodiment and are not intended to limit the scope of the invention. The distal end outer hub 122 is "outer" relative to the distal end inner hub 58 of the support arm 50 in the sense that the vertically orientated side walls 202 of the distal end outer hub 122 are on the outside of the distal end inner hub 58. Similarly, the proximal end outer hub 120 is "outer" relative to the proximal end inner hub 56 of the support arm 50 in the sense that the vertically orientated side walls 156 of the proximal end outer hub 120 are on the outside of the proximal end inner hub 56.

Also in the above described load balancing arm 20, the proximal end outer hub 120 and the load adjustment base 114 need not be separate components and instead can constitute a single manufactured component whether by casting and subsequent subtractive manufacturing techniques or by additive manufacturing techniques such as 3D printing or the like.

Thus, in a more general sense, the load balancing arm 20 may include a proximal hub 120, 114 configured for pivotable movement about an axis P-P; a support arm 50 having a proximal end and a distal end, the proximal end of the support arm 50 being pivotably mounted to the proximal hub 120, 114 about a support arm proximal end pivot axis 62; a link 90 having a proximal end and a distal end, the proximal end of the link 90 being pivotably mounted to the proximal hub 120, 114 about a link proximal end pivot axis 92; a distal end vertical block 112 pivotably mounted to the distal end of the support arm 50 about a support arm distal end pivot axis 60 and pivotably mounted to the distal end of the link 90 about a link distal end pivot axis 94; and a distal hub 122 configured to support a medical device load 36 for pivotable movement about an axis D-D; wherein the distal hub 122 is mounted to the distal end vertical block 112 for pivotable movement between a first position in which the axis D-D is at a first angle relative to the axis P-P and a second position in which the axis D-D is at a second angle relative to the axis P-P, wherein the first angle is different than the second angle. In such case, the proximal hub 120, 114, the support arm 50, the link 90, and the distal end vertical block 112 may form the four bar linkage.

The above described load balancing arm 20 is described as having four links including a Link A constituted by a support arm 50, a Link B constituted by a link assembly 90 or merely a link 90, a Link X constituted by the distal end vertical block 112, and a Link Y constituted by the load adjustment base 114 or the proximal end outer hub 120 secured to the load adjustment base 114. The load balancing arm 20 may be constructed of any suitable structural components to constitute the respective Links A, B, X and Y, and other embodiments are contemplated. For example, the load adjustment base 114 may not provide a load adjustment capability and instead may be a proximal end vertical block. In this regard, the terms support arm 50, link assembly 90, distal end vertical block 112, and load adjustment base 114 are used to facilitate understanding of the illustrative embodiment and are not intended to limit the scope of the invention.

In a more general sense, then, the load balancing arm 20 may include a four bar linkage comprising lateral Links A and B, and upright Links X and Y at opposite ends of the lateral Links A and B; the Link Y being configured for pivotable movement about an axis P-P; a distal hub 122 configured to support a payload such as a medical device load for pivotable movement about an axis D-D; wherein the distal hub 122 is mounted to the Link X for pivotable movement between a first position in which the axis D-D is at a first angle relative to the axis P-P and a second position in which the axis D-D is at a second angle relative to the axis P-P, wherein the first angle is different than the second angle. For such a load balancing arm 20, the Link A has a proximal end and a distal end, the proximal end of the Link A being pivotably mounted to the Link Y about a Link A proximal end pivot axis 62; the Link B has a proximal end and a distal end, the proximal end of the Link B being pivotably mounted to the Link Y about a Link B proximal end pivot axis 92; and the Link X is pivotably mounted to the distal end of the Link A about a Link A distal end pivot axis 60 and pivotably mounted to the distal end of the Link B about a Link B distal end pivot axis 94.

Figure 13:
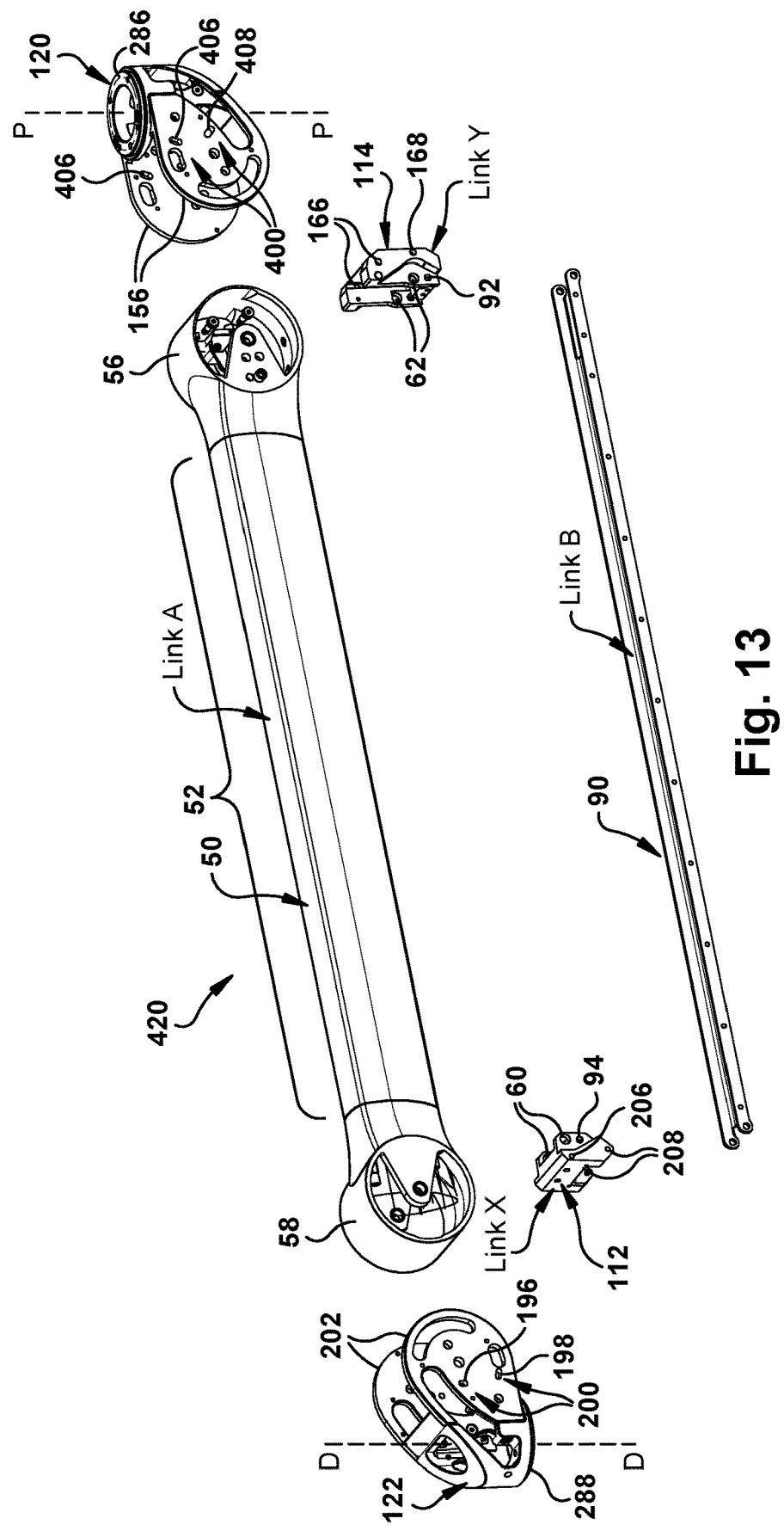
FIG. 13 is an exploded isometric view of proximal and distal end outer hubs separated from the Links X, A, B, Y, of a load balancing arm according to another embodiment.
Figure 14:
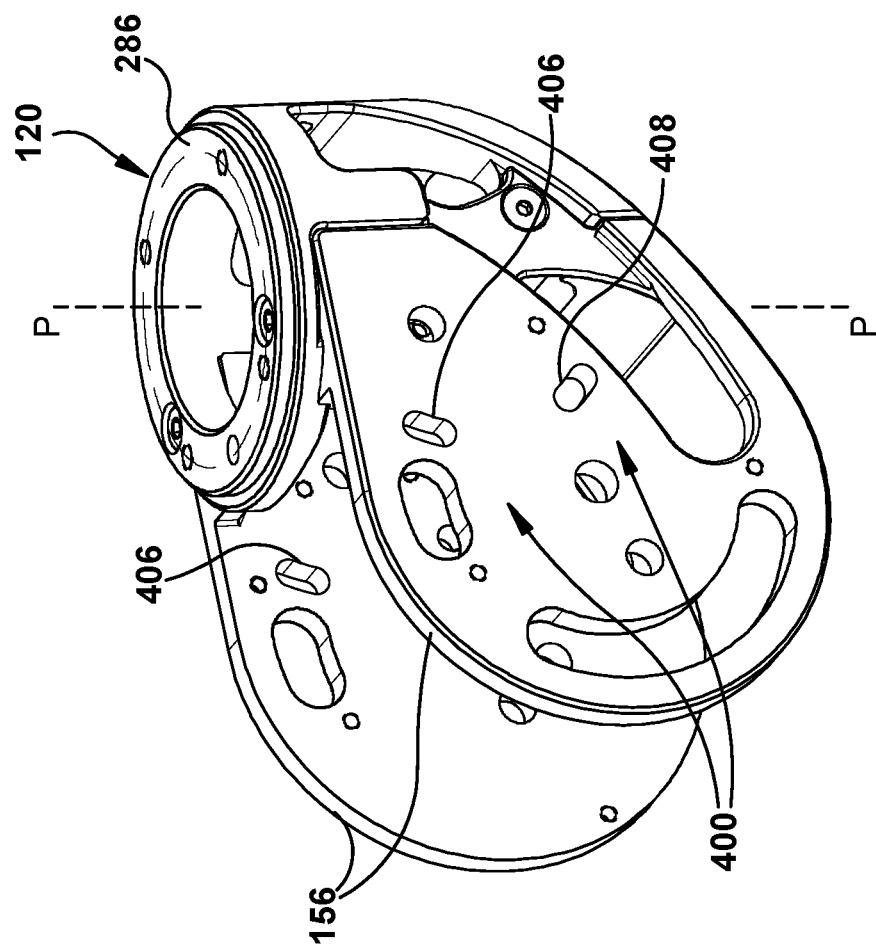
FIG. 14 is an isolated isometric view of the proximal end outer hub of the FIG. 13 load balancing arm, showing arc shape slot openings therein.

In the above described load balancing arm 20, the parallelism adjustment mechanism 200 is located at the distal end of the load balancing arm 20; that is, the distal end outer hub 122 is pivotably adjustable relative to the distal end vertical block 112 by means of the slot openings 196, 198 being moved along the fasteners 176, 178 (when loosened), and the proximal end outer hub 120 is secured to the load adjustment base 114 without pivotable adjustability as the fasteners 136, 138 are inserted through the through-holes 146, 148 in the proximal end outer hub 120 rather than slot openings. In an alternate embodiment, as shown in FIGS. 13 and 14, a parallelism adjustment mechanism 400 may be located at the proximal end of a load balancing arm 420. Thus, for example, the threaded-holes 146, 148 in the proximal end outer hub 120 may be replaced with slot openings 406, 408 and configured in a manner similar to the slot openings 196, 198 described above with respect to the distal end outer hub 122. The proximal end outer hub 120 may be pivotably adjustable relative to the load adjustment base 114 by means of the slot openings 406, 408 being moved along the fasteners 136, 138 extending through the slot openings 406, 408 (when loosened), similar to the fasteners 176, 178 extending through the slot openings 196, 198 in the parallel adjustment mechanism 200.

In a more general sense, the load balancing arm 420 equipped with a parallelism adjustment mechanism 400 at its proximal end may include, for example, a distal hub 122 configured to support a medical device load for pivotable movement about an axis D-D; a support arm 50 having a proximal end and a distal end, the distal end of the support arm 50 being pivotably mounted to the distal hub 122 about a support arm distal end pivot axis 60; a link 90 having a proximal end and a distal end, the distal end of the link 90 being pivotably mounted to the distal hub 122 about a link distal end pivot axis 94; a proximal end vertical block 114 pivotably mounted to the proximal end of the support arm 50 about a support arm proximal end pivot axis 62 and pivotably mounted to the proximal end of the link 90 about a link proximal end pivot axis 92; and a proximal hub 120 configured for pivotable movement about an axis P-P; wherein the proximal hub 120 is mounted to the proximal end vertical block 114 for pivotable movement between a first position in which the axis D-D is at a first angle relative to the axis P-P and a second position in which the axis D-D is at a second angle relative to the axis P-P, wherein the first angle is different than the second angle.

In another embodiment, a support arm 420 for supporting a payload may include a four bar linkage comprising lateral Links A and B, and upright Links X and Y at opposite ends of the lateral Links A and B; a proximal hub 120 configured for pivotable movement about an axis P-P; the Link X being configured to support the payload for pivotable movement about an axis D-D; wherein the proximal hub 120 is mounted to the Link Y for pivotable movement between a first position in which the axis D-D is at a first angle relative to the axis P-P and a second position in which the axis D-D is at a second angle relative to the axis P-P, wherein the first angle is different than the second angle. The Link A may have a proximal end and a distal end, the proximal end of the Link A being pivotably mounted to the Link Y about a Link A proximal end pivot axis. The Link B may have a proximal end and a distal end, the proximal end of the Link B being pivotably mounted to the Link Y about a Link B proximal end pivot axis. The Link X may be pivotably mounted to the distal end of the Link A about a Link A distal end pivot axis and pivotably mounted to the distal end of the Link B about a Link B distal end pivot axis.

A method of adjusting an angle of a distal hub 122 of a load balancing arm 20 relative to a proximal hub 120, 114 of the load balancing arm 20 will now be described. In one step, a load balancing arm 20 is provided that has a proximal hub 120, 114, a support arm 50, a link 90, and a distal end vertical block 112, wherein the proximal hub 120, 114, the support arm 50, the link 90, and the distal end vertical block 112 form a four bar linkage. The proximal hub 120, 114 may be configured for pivotable movement about an axis P-P. In another step, a distal hub 122 is provided that is configured to support a medical device load 36 for pivotable movement about an axis D-D. In another step, the distal hub 122 is mounted to the distal end vertical block 112 for pivotable movement between a first position in which the axis D-D is at a first angle relative to the axis P-P and a second position in which the axis D-D is at a second angle relative to the axis P-P, wherein the first angle is different than the second angle.

In another step, the medical device load 36 is mounted to the distal hub 122 for pivotable movement about the axis D-D. In another step, the pivotably moving the distal hub 122 includes moving a slot opening 196, 198 in the distal hub 122 along a fastener 176, 178 projecting from the distal end vertical block 112 into the slot opening 196, 198. In another step, the fastener 176, 178 is fastened into a threaded hole 206, 208 in the distal end vertical block 112 until a head of the fastener 206, 208 engages the distal hub 122 on opposite sides of the slot opening 196, 198 to secure the distal hub 122 to the distal end vertical block 112. In another step, the fastener 206, 208 is a serrated flange screw and the threading includes tightening the serrated flange screw to a predetermined torque to displace some material in the distal hub 122 to create a mechanical interference lock between a head of the serrated flange screw and the distal hub 122.

As will be appreciated, the parallelism adjustment mechanism 200 provides a permanent mechanical alignment adjustment at system assembly that allows for relaxation of manufacturing component part tolerances, for example manufacturing tolerances in the support arm 50 and the link assembly 90. The parallelism adjustment mechanism 200 uses very few parts and in some embodiments no additional parts from that required for a load balancing arm equipped without such parallelism adjustment mechanism 200. The parallelism adjustment mechanism 200 provides slot openings 196, 198 for attaching the distal hub 122 to the distal end vertical block 112 that allow angular adjustment to compensate for out of parallel conditions caused by stack up of manufacturing tolerances on components that make up the four bar linkage. The parallelism adjustment mechanism 200 provides fasteners 176, 178 such as shoulder screws or serrated flange screws to lock the distal hub 122 into position when it is adjusted to level preventing rotational slippage from torque applied to the joint. Serrated flange screws provide a mechanical interference lock in addition to a frictional lock.

As will be appreciated, the parallelism adjustment mechanism 400 provides a permanent mechanical alignment adjustment at system assembly that allows for relaxation of manufacturing component part tolerances, for example manufacturing tolerances in the support arm 50 and the link assembly 90. The parallelism adjustment mechanism 400 uses very few parts and in some embodiments no additional parts from that required for a load balancing arm equipped without such parallelism adjustment mechanism 400. The parallelism adjustment mechanism 400 provides slot openings 406, 408 for attaching the proximal hub 120 to the proximal end vertical block 114 that allow angular adjustment to compensate for out of parallel conditions caused by stack up of manufacturing tolerances on components that make up the four bar linkage. The parallelism adjustment mechanism 400 provides fasteners 176, 178 such as shoulder screws or serrated flange screws to lock the proximal hub 120 into position when it is adjusted to level preventing rotational slippage from torque applied to the joint. Serrated flange screws provide a mechanical interference lock in addition to a frictional lock.

It will further be appreciated that both the parallelism adjustment mechanism 200 and the parallelism adjustment mechanism 400 may be incorporated into a single support arm. In other words, a support arm may have either or both the parallelism adjustment mechanism 200 and the parallelism adjustment mechanism 400.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A load balancing arm for a medical device support system, comprising:

a proximal hub configured for pivotable movement about an axis P-P;

a support arm having a proximal end and a distal end, the proximal end of the support arm being pivotably mounted to the proximal hub about a support arm proximal end pivot axis;

a link having a proximal end and a distal end, the proximal end of the link being pivotably mounted to the proximal hub about a link proximal end pivot axis;

a distal end vertical block pivotably mounted to the distal end of the support arm about a support arm distal end pivot axis and pivotably mounted to the distal end of the link about a link distal end pivot axis; and a distal hub configured to support a medical device load for pivotable movement about an axis D-D;

wherein the distal hub is mounted to the distal end vertical block for pivotable movement between a first position in which the axis D-D is at a first angle relative to the axis P-P and a second position in which the axis D-D is at a second angle relative to the axis P-P, wherein the first angle is different than the second angle.

2. The load balancing arm of claim 1, wherein the proximal hub, the support arm, the link, and the distal end vertical block form a four bar linkage.

3. The load balancing arm of claim 1, wherein the distal hub is mounted to the distal end vertical block for pivotable movement about the support arm distal end pivot axis.

4. The load balancing arm of claim 1, wherein the support arm proximal end pivot axis and the link proximal end pivot axis are substantially vertically aligned and the support arm distal end pivot axis and the link distal end pivot axis are substantially vertically aligned.

5. The load balancing arm of claim 1, wherein when the distal hub is in the first position the axis D-D is not parallel to the axis P-P and when the distal hub is in the second position the axis D-D is substantially parallel to the axis P-P.

6. The load balancing arm of claim 1, wherein the axis P-P is a vertical axis P-P and wherein when the distal hub is in the second position the axis D-D is a predetermined amount of degrees offset from the vertical axis P-P to compensate for assembly deflection resulting from the medical device load.

7. The load balancing arm of claim 1, wherein the distal hub includes a slot opening and wherein the distal end vertical block has a fastener projecting therefrom that extends into the slot opening, and wherein the distal hub is configured such that as the distal hub is pivotably moved from the first position to the second position the slot opening moves along the fastener projecting therein.

8. The load balancing arm of claim 7, wherein opposite ends of the slot opening define maximum pivotable movement of the distal hub relative to the distal end vertical block.

9. The load balancing arm of claim 7, wherein the fastener is a threaded fastener and the distal end vertical block has a threaded hole for threadingly receiving the fastener, and wherein the fastener has a head that is sufficiently wide to bridge the slot opening and that is configured when tightened to engage the distal hub on opposite sides of the slot opening to secure the distal hub to the distal end vertical block.

10. The load balancing arm of claim 7, wherein the fastener secures the distal hub to the distal end vertical block by means of friction provided by a clamp load of the fastener head exerted on the distal hub.

11. The load balancing arm of claim 7, wherein the fastener is a serrated flange screw and the size of the serrated flange screw and the materials of the serrated flange screw and distal hub are selected so that the serrated flange screw when tightened to a predetermined torque displaces some material in the distal hub to create a mechanical interference lock between a head of the serrated flange screw and the distal hub.

12. The load balancing arm of claim 1, wherein the support arm includes a support arm proximal end hub and a support arm distal end hub and an intermediate beam between the support arm proximal end hub and the support arm distal end hub, the support arm proximal end hub being pivotably mounted to the proximal hub, the distal end vertical block being pivotably mounted to the support arm distal end hub.

13. The load balancing arm of claim 12, wherein the intermediate beam has a cavity, and the support arm includes at least one tension member that extends through the cavity of the intermediate beam and is secured at opposite ends to the support arm proximal end hub and the support arm distal end hub, the tension member securing the support arm proximal end hub, the support arm distal end hub, and the intermediate beam together.

14. A support arm for supporting a payload, comprising:
a four bar linkage comprising lateral Links A and B, and upright Links X and Y at opposite ends of the lateral Links A and B;
the Link Y being configured for pivotable movement about an axis P-P;
a distal hub configured to support the payload for pivotable movement about an axis D-D;
wherein the distal hub is mounted to the Link X for pivotable movement between a first position in which the axis D-D is at a first angle relative to the axis P-P and a second position in which the axis D-D is at a second angle relative to the axis P-P, wherein the first angle is different than the second angle.

15. The support arm of claim 14, wherein
the Link A has a proximal end and a distal end, the proximal end of the Link A being pivotably mounted to the Link Y about a Link A proximal end pivot axis;
the Link B has a proximal end and a distal end, the proximal end of the Link B being pivotably mounted to the Link Y about a Link B proximal end pivot axis; and
the Link X is pivotably mounted to the distal end of the Link A about a Link A distal end pivot axis and pivotably mounted to the distal end of the Link B about a Link B distal end pivot axis.

16. A medical device support system, comprising:
a shaft;
an extension arm mounted to the shaft for rotational movement about the shaft; and
a load balancing arm including:
a proximal hub mounted to the extension arm for pivotable movement about an axis P-P;
a support arm having a proximal end and a distal end, the proximal end of the support arm being pivotably mounted to the proximal hub about a support arm proximal end pivot axis;
a link having a proximal end and a distal end, the proximal end of the link being pivotably mounted to the proximal hub about a link proximal end pivot axis;
a distal end vertical block pivotably mounted to the distal end of the support arm about a support arm distal end pivot axis and pivotably mounted to the distal end of the link about a link distal end pivot axis; and
a distal hub configured to support a medical device load for pivotable movement about an axis D-D;
wherein the distal hub is mounted to the distal end vertical block for pivotable movement between a first position in which the axis D-D is at a first angle relative to the axis P-P and a second position in which the axis D-D is at a second angle relative to the axis P-P, wherein the first angle is different than the second angle.

17. A method of adjusting an angle of a distal hub of a load balancing arm relative to a proximal hub of the load balancing arm, comprising:
providing a load balancing arm having a proximal hub, a support arm, a link, and a distal end vertical block, wherein the proximal hub, the support arm, the link, and the distal end vertical block form a four bar linkage;

wherein the proximal hub is configured for pivotable movement about an axis P-P;

providing a distal hub configured to support a medical device load for pivotable movement about an axis D-D; and mounting the distal hub to the distal end vertical block for pivotable movement between a first position in which the axis D-D is at a first angle relative to the axis P-P and a second position in which the axis D-D is at a second angle relative to the axis P-P, wherein the first angle is different than the second angle.

18. The method of claim 17, comprising mounting a medical device load to the distal hub for pivotable movement about the axis D-D.

19. The method of claim 17, wherein pivotably moving the distal hub includes moving a slot opening in the distal hub along a fastener projecting from the distal end vertical block into the slot opening.

20. The method of claim 19, threading the fastener into a threaded hole in the distal end vertical block until a head of the fastener engages the distal hub on opposite sides of the slot opening to secure the distal hub to the distal end vertical block.

21. The method of claim 20, wherein the fastener is a serrated flange screw and the threading includes tightening the serrated flange screw to a predetermined torque to displace some material in the distal hub to create a mechanical interference lock between a head of the serrated flange screw and the distal hub.

* * * * *